US012097135B2

(12) United States Patent
Raaz et al.

(10) Patent No.: US 12,097,135 B2
(45) Date of Patent: *Sep. 24, 2024

(54) METHODS, DEVICES, AND COMPOSITIONS FOR TREATING VASCULAR ANEURYSMS

(71) Applicant: Board of Trustees of the Leland Stanford Junior University, Palo Alto, CA (US)

(72) Inventors: Uwe Raaz, Leipzig (DE); Isabel Schellinger, Leipzig (DE); Joshua Spin, San Jose, CA (US); Philip Tsao, Los Altos, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 694 days.

This patent is subject to a terminal disclaimer.

(21) Appl. No.: 17/028,048

(22) Filed: Sep. 22, 2020

(65) Prior Publication Data

US 2021/0059843 A1     Mar. 4, 2021

Related U.S. Application Data

(63) Continuation of application No. 15/070,817, filed on Mar. 15, 2016, now Pat. No. 10,779,964.
(Continued)

(51) Int. Cl.
*A61F 2/82*     (2013.01)
*A61B 17/00*     (2006.01)
*A61F 2/90*     (2013.01)

(52) U.S. Cl.
CPC .......... *A61F 2/82* (2013.01); *A61B 17/00491* (2013.01); *A61F 2/90* (2013.01);
(Continued)

(58) Field of Classification Search
None
See application file for complete search history.

(56) References Cited

U.S. PATENT DOCUMENTS

2007/0282422 A1    12/2007   Biggs et al.
2009/0177267 A1    7/2009   Biggs et al.
(Continued)

OTHER PUBLICATIONS

Raaz, Uwe et al. "Segmental Aortic Stiffening Contributes to Experimental Abdominal Aortic Aneurysm Development" Circulation. May 19, 2015; 131(20): 1783-1795. doi:10.1161/CIRCULATIONAHA .114.012377. (Year: 2015).*
(Continued)

*Primary Examiner* — Shaun L David
(74) *Attorney, Agent, or Firm* — Fredrikson & Byron, P.A.

(57) ABSTRACT

Methods, compositions, and devices for treating a vascular aneurysm, including an abdominal aortic aneurysm, are disclosed. In particular, the various embodiments relate to a method of treating an abdominal aortic aneurysm by increasing the mechanical stiffness of an aortic segment adjacent to the abdominal aortic aneurysm in a subject. The mechanical stiffness of the adjacent aortic segment may be increased, for example, by applying a surgical adhesive or intravascular stent. Such treatment reduces stress on the aortic wall and limits further growth of the abdominal aortic aneurysm.

25 Claims, 17 Drawing Sheets
(9 of 17 Drawing Sheet(s) Filed in Color)

Related U.S. Application Data

(60) Provisional application No. 62/133,450, filed on Mar. 15, 2015.

(52) U.S. Cl.
CPC ............... *A61B 2017/00778* (2013.01); *A61F 2002/823* (2013.01)

(56) References Cited

U.S. PATENT DOCUMENTS

| | | |
|---|---|---|
| 2009/0214654 A1 | 8/2009 | Isenburg et al. |
| 2010/0016833 A1 | 1/2010 | Ogle et al. |

OTHER PUBLICATIONS

Cocciolone et al., "Elastin, arterial mechanics, and cardiovascular disease", Apr. 2018, pp. H189-H205, vol. 315, Issue 2, Publisher: American Physiological Society.

Wagenhauser et al., "Chronic Nicotine Exposure Induces Murine Aortic Remodeling and Stiffness Segmentation—Implications for Abdominal Aortic Aneurysm Susceptibility", "Original Research", Oct. 2018, vol. 9, No. 1459, Publisher: Frontiers in Physiology.

\* cited by examiner

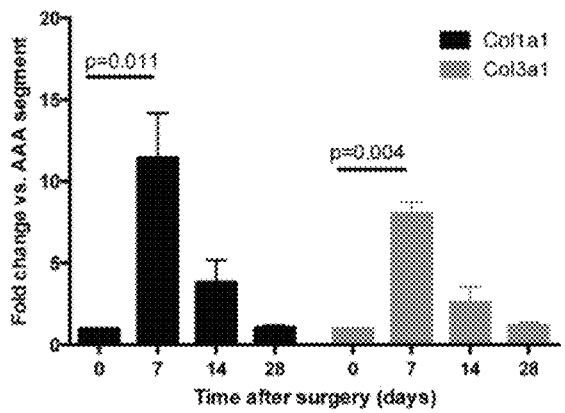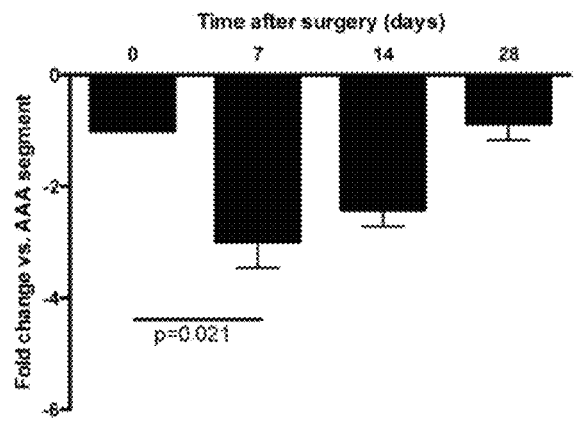
FIG. 8A　　　　　　　　　　　　　FIG. 8B
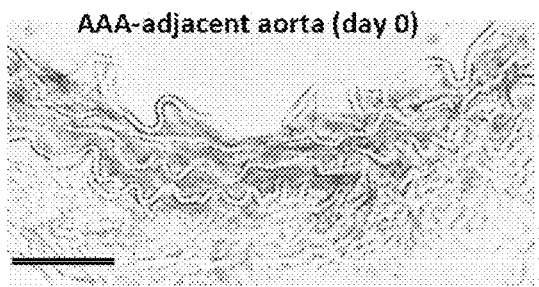
FIG. 8C
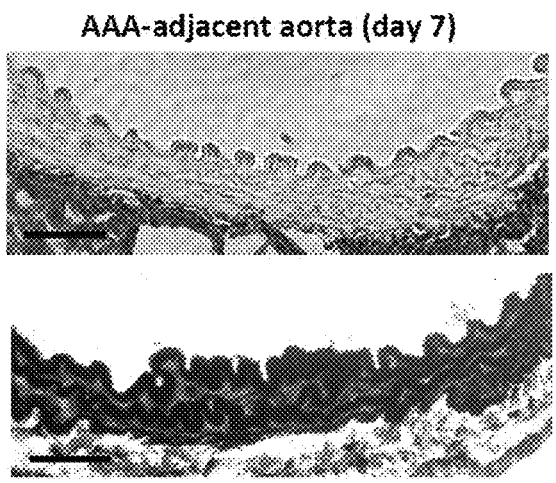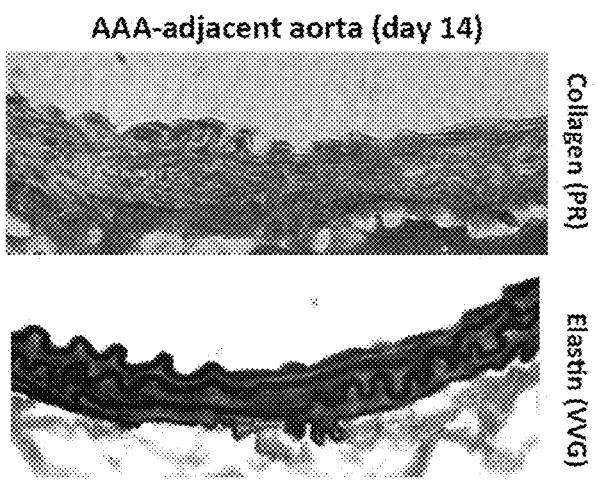
FIG. 8D

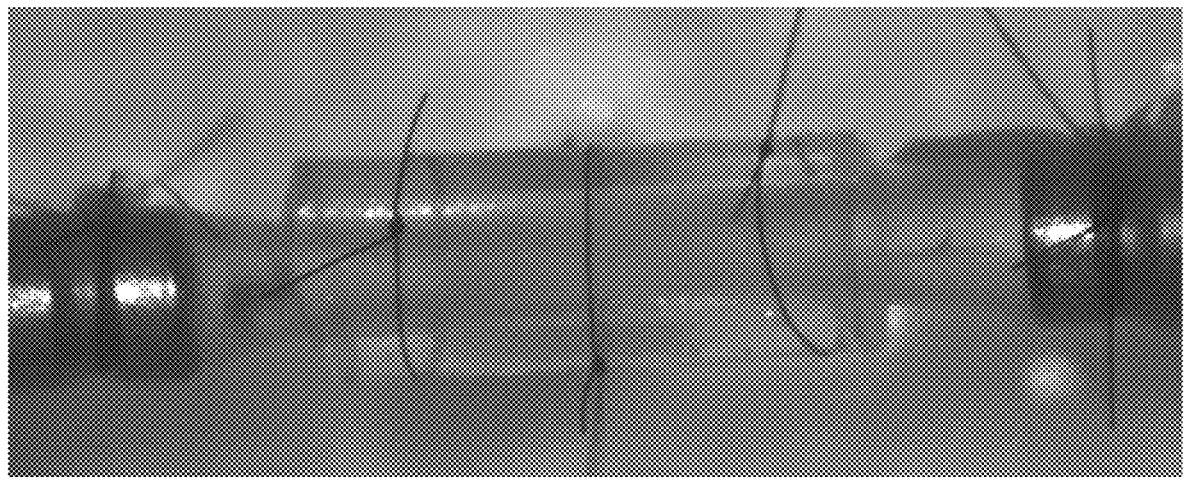
FIG. 13
 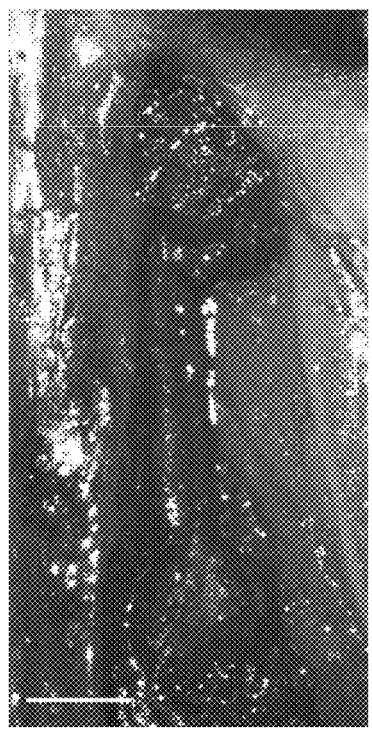
FIG. 14A          FIG. 14B

METHODS, DEVICES, AND COMPOSITIONS FOR TREATING VASCULAR ANEURYSMS

CROSS-REFERENCE TO RELATED APPLICATION(S)

This application claims priority as a continuation to U.S. patent application Ser. No. 15/070,817, filed Mar. 15, 2016, and entitled "Methods, Devices, and Compositions for Treating Abdominal Aortic Aneurysms," which claims priority under 35 U.S.C. § 119(e) to U.S. Provisional Application 62/133,450, filed Mar. 15, 2015, and entitled "Methods of Treating Abdominal Aortic Aneurysms," which is hereby incorporated herein by reference in its entirety.

GOVERNMENT SUPPORT

This invention was made with Government support under contract 1R01HL105299 awarded by the National Institutes of Health. The Government has certain rights in this invention.

FIELD OF THE INVENTION

The various embodiments herein relate generally to methods of treating an abdominal aortic aneurysm (also referred to herein as an "AAA"). In particular, the implementations relate to methods, devices, and compositions for treating AAA disease by increasing the mechanical stiffness of an aortic segment adjacent to an abdominal aortic aneurysm in a subject.

BACKGROUND OF THE INVENTION

Abdominal aortic aneurysm carries a high mortality in case of rupture. Current therapies are limited to open surgical or interventional stent-based exclusion of the aneurysmal sac from the circulation in order to prevent rupture. However, these treatment options are generally reserved for larger aneurysms (typically AAA diameter greater than 5.5 cm), and there is no effective therapy targeting the evolution of small aneurysms. The lack of treatment options partly derives from an insufficient understanding of early AAA pathogenesis.

Recent evidence suggests that AAA formation is not simply due to aortic wall degeneration, resulting in passive lumen dilation, but to active, dynamic remodeling. The latter involves transmural inflammation, extracellular matrix ("ECM") alterations including elastin fragmentation and (compensatory) collagen deposition, vascular smooth muscle cell (VSMC) apoptosis, and oxidative stress.

From a patho-mechanistic point of view, it is essential not only to characterize the particular cellular and molecular alterations involved in AAA formation, but also to identify early triggers of remodeling.

There remains a need for better methods of treating AAA, particularly at early stages of disease.

BRIEF SUMMARY OF THE INVENTION

Discussed herein are various methods of treating an abdominal aortic aneurysm. Other embodiments relate to methods of treating any type of vascular aneurysm, including, for example, thoracic aortic aneurysms.

In one aspect, the invention includes a method of treating a subject for an abdominal aortic aneurysm, the method comprising increasing the mechanical stiffness of an aortic segment adjacent to the abdominal aortic aneurysm in the subject. In one embodiment, increasing the mechanical stiffness of the aortic segment comprises applying a surgical adhesive locally to the aortic segment. In another embodiment, increasing the mechanical stiffness of the aortic segment comprises deploying an intravascular stent that stiffens the aortic segment. The subject may have early stage, intermediate stage, or late stage AAA disease, wherein the treatment reduces the growth of an abdominal aortic aneurysm compared to in the absence of the treatment. The subject may further show decreased inflammation, apoptosis, or reactive oxygen species in the abdominal aorta as a result of the treatment.

In another aspect, the invention includes a method of minimizing growth of an abdominal aortic aneurysm in a subject, the method comprising increasing the mechanical stiffness of an aortic segment adjacent to the abdominal aortic aneurysm.

More specifically, in Example 1, a method of treating a subject for an abdominal aortic aneurysm comprises increasing the mechanical stiffness of an aortic segment adjacent to the abdominal aortic aneurysm in the subject.

Example 2 relates to the method according to Example 1, wherein increasing the mechanical stiffness of the aortic segment comprises applying a surgical adhesive locally to the aortic segment.

Example 3 relates to the method according to Example 1, wherein increasing the mechanical stiffness of the aortic segment comprises deploying an intravascular stent that stiffens the aortic segment.

Example 4 relates to the method according to Example 1, wherein growth of the abdominal aortic aneurysm is reduced compared to in the absence of treating the subject.

Example 5 relates to the method according to Example 1, wherein the subject shows decreased inflammation in the abdominal aorta compared to in the absence of treating the subject.

Example 6 relates to the method according to Example 1, wherein the subject shows decreased apoptosis in the abdominal aorta compared to in the absence of treating the subject.

Example 7 relates to the method according to Example 1, wherein the subject shows decreased production of reactive oxygen species in the abdominal aorta compared to in the absence of treating the subject.

Example 8 relates to the method according to Example 1, wherein the subject has an early stage abdominal aortic aneurysm.

Example 9 relates to the method according to Example 1, wherein the diameter of the abdominal aortic aneurysm is less than 5.5 cm.

In Example 10, a method of minimizing growth of an abdominal aortic aneurysm in a subject comprises increasing the mechanical stiffness of an aortic segment adjacent to the abdominal aortic aneurysm.

Example 11 relates to the method according to Example 10, wherein increasing the mechanical stiffness of the aortic segment comprises applying a surgical adhesive locally to the aortic segment.

Example 12 relates to the method according to Example 10, wherein growth of the abdominal aortic aneurysm is reduced compared to in the absence of increasing the mechanical stiffness of the aortic segment.

Example 13 relates to the method according to Example 10, wherein the subject shows decreased inflammation in the abdominal aorta compared to in the absence of increasing the mechanical stiffness of the aortic segment.

Example 14 relates to the method according to Example 10, wherein the subject shows decreased apoptosis in the abdominal aorta compared to in the absence of increasing the mechanical stiffness of the aortic segment.

Example 15 relates to the method according to Example 10, wherein the subject shows decreased production of reactive oxygen species in the abdominal aorta compared to in the absence of increasing the mechanical stiffness of the aortic segment.

Example 16 relates to the method according to Example 10, wherein the subject has an early stage abdominal aortic aneurysm.

Example 17 relates to the method according to Example 10, wherein the diameter of the abdominal aortic aneurysm is less than 5.5 cm.

In Example 18, a method of treating an abdominal aortic aneurysm comprises positioning a stiffening device or stiffening composition at at least one aneurysm-adjacent aortic segment, whereby the stiffening device or stiffening composition increases the mechanical stiffness of the aneurysm-adjacent aortic segment.

Example 19 relates to the method according to Example 18, wherein the stiffening composition comprises a surgical adhesive, wherein the positioning the stiffening composition further comprises applying the surgical adhesive to an outer surface of the aneurysm-adjacent aortic segment.

Example 20 relates to the method according to Example 18, wherein the stiffening device comprises an intravascular stent, wherein the positioning the stiffening device further comprises deploying the intravascular stent into a lumen of the aneurysm-adjacent aortic segment.

These and other embodiments will readily occur to those of skill in the art in view of the disclosure herein. While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A is a bar graph depicting temporal analysis of the Col1a1 and Col3a1 gene expression in the AAA-adjacent aorta compared to the AAA (PPE-treated) segment.

FIG. 8B is a bar graph depicting temporal analysis of miR-29b expression in the AAA-adjacent aorta compared to the AAA (PPE-treated) segment.

FIG. 8C is a set of images depicting in situ hybridization for miR-29b (purple-blue dye) and red nuclear counterstain in the AAA-adjacent aortic segments (original magnification 400×, scale bar 50 µm) at day 0 and day 7.

FIG. 8D is a set of images depicting the aortic wall taken from AAA-adjacent aortic segments 7 days or 14 days after PPE-treatment, with the upper panels showing the segments stained with Picrosirius Red (red: collagen; yellow: muscle) and the lower panels showing the segments stained with Elastin VVG staining.

FIG. 11A-1 depicts an unrestrained/unstiffened aorta upon which cyclic strain is imposed in Example 1 as described below.

FIG. 11A-2 depicts a completely restrained aorta upon which cyclic strain is imposed in Example 1 as described below.

FIG. 11A-3 depicts a segmentally restrained aorta upon which cyclic strain is imposed in Example 1 as described below.

FIG. 13 depicts the setup for differential mechanical stimulation of the murine aorta ex vivo in Example 1 as described below.

FIG. 14A is a photograph of the abdominal aorta before glue application.

FIG. 14B is a photograph of the abdominal aorta after glue application to the segments adjacent to the PPE-treated segment, as described in Example 1 below.

DETAILED DESCRIPTION

The various embodiments disclosed or contemplated herein relate to methods, systems, and devices for treating an abdominal aortic aneurysm. More specifically, the various implementations involve treating an abdominal aortic aneurysm in a subject by increasing the mechanical stiffness of an aortic segment adjacent to the aneurysm, thereby reducing the stress to the aortic wall and limiting further growth of the aneurysm. The mechanical stiffness of the adjacent aortic segment may be increased, in one exemplary embodiment, by applying a surgical adhesive to the segment. Alternatively, the mechanical stiffness of the adjacent segment can be increased by implanting an intravascular stent. Other embodiments relate to treatment of any type of vascular aneurysm, including, for example, thoracic aortic aneurysms, wherein the treatment includes increasing the mechanical stiffness of adjacent vascular segments according to, or in similar fashion to, the various methods, devices, and compositions disclosed or contemplated herein.

Figure 1:
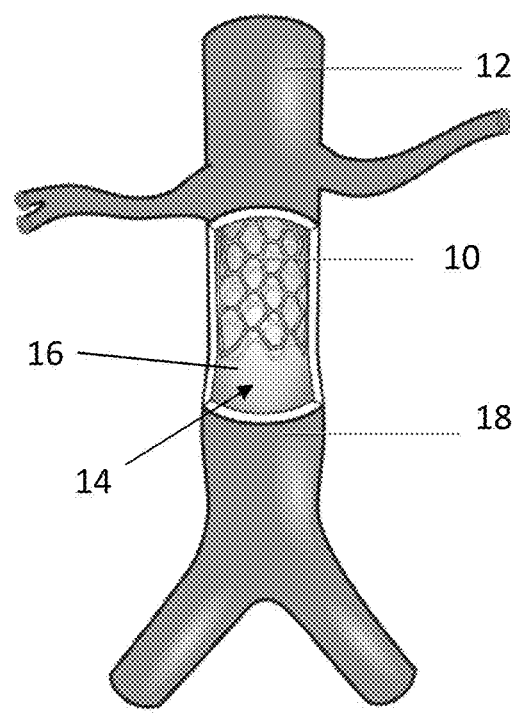
FIG. 1 is a front, cutaway view of an intravascular stent positioned in an aorta, according to one embodiment.

According to one embodiment, FIG. 1 depicts an intravascular stent 10 disposed within the abdominal aorta 12. The stent 10 is disposed within the lumen 14 of the aorta 12 and adjacent to the aortic aneurysm 18 as shown. In this specific exemplary embodiment, the stent 10 is positioned adjacent to and upstream from the aneurysm 18. Alternatively, the stent 10 can be positioned adjacent to and downstream from the aneurysm 18. In a further alternative, two stents could be used with one positioned adjacent to and upstream from the aneurysm 18 and the other positioned adjacent to and downstream from the aneurysm 18. In certain implementations, the stent 10 an expandable stent 10 that is configured to expand into contact with the inner wall 16 of the aorta, thereby providing support and mechanical stiffness to the length of aorta 12 with which the stent 10 is in contact. In one implementation, the stent 10 is a deployable stent 10 that is implanted via a known non-invasive procedure. Alternatively, the stent 10 can be any known stent for providing mechanical intravascular support that can be implanted by any known procedure.

Figure 2:
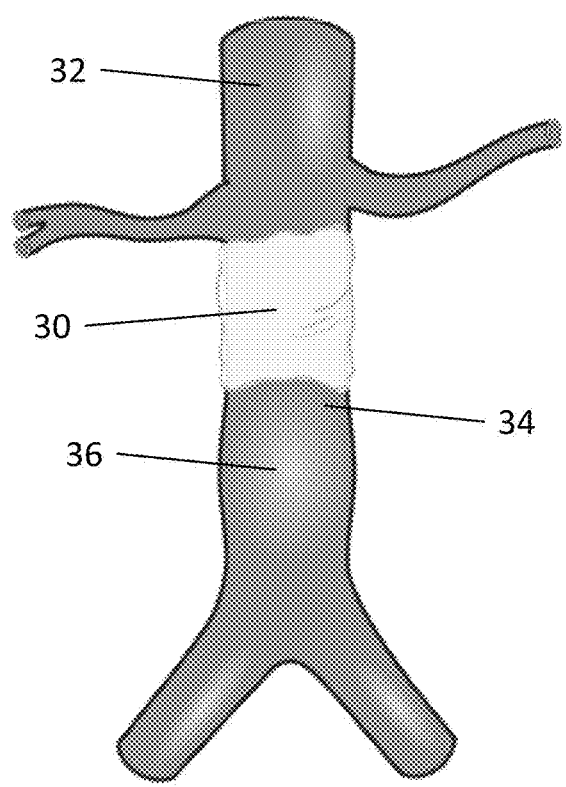
FIG. 2 is a front view of a surgical adhesive applied to an outer surface of an aorta, according to another embodiment.

FIG. 2 depicts a surgical adhesive 30 applied to or disposed on an outer wall 34 of an aorta 32, according to another implementation. In one embodiment, the adhesive 30 is a surgical adhesive or surgical glue (also referred to herein as "adhesive" or "gel"). In one specific example, the adhesive 30 is BioGlue™, which can be purchased from CryoLife, Inc., in Kennesaw, GA. Alternatively, the adhesive 30 can be any known medical composition that can be applied to human tissue and subsequently harden. In this specific exemplary embodiment, the adhesive 30 is disposed adjacent to and upstream from the aneurysm 36. Alternatively, the adhesive 30 can be positioned adjacent to and downstream from the aneurysm 36. In a further alternative, the adhesive 30 can be positioned in two locations, with adhesive 30 applied adjacent to and upstream from the aneurysm 36 and further applied adjacent to and downstream from the aneurysm 36 as well. In use, the adhesive 30 is applied to the outer wall 34 of the aorta 32 and then allowed to harden, thereby providing mechanical stiffness to the length of aorta 32 that the adhesive 30 is disposed along. The adhesive 30 can be applied by any known procedure for applying an adhesive to an outer wall of a blood vessel.

As mentioned above, either of the two devices, compositions, or methods depicted in FIGS. 1-2 and discussed above can be used to treat an abdominal aortic aneurysm. More specifically, each of the stent 10 and the adhesive 30 are positioned as described above to increase the mechanical stiffness of the aortic segment along which they are positioned adjacent to the aneurysms 18, 36 respectively. As such, the stent 10 and the adhesive 30 are each positioned along the aorta to reduce the stress to the aortic wall and limit further growth of the aneurysm 18, 36 respectively.

Without being limited by theory, it is believed that each of these interventional mechanical stiffening instruments (10, 30, respectively) positioned adjacent to an abdominal aortic aneurysm are effective in limiting the growth of the aneurysm (18, 36, respectively) by limiting the remodeling and expansion of the aneurysm and thereby forestalling or eliminating the need for surgical repair.

It is known that abdominal aortic aneurysm ("AAA") formation is accompanied by increased stiffness of the aneurysmal vessel segment compared to the normal aorta, also called segmental aortic stiffening ("SAS"). Aneurysmal stiffening occurs due to profound changes in extracellular matrix ("ECM") organization including elastin fragmentation and enhanced adventitial collagen deposition and turnover. It is believed that the segmental aortic stiffening is a pathogenetic factor contributing to the development of an abdominal aortic aneurysm. That is, degenerative stiffening of the aneurysm-prone aortic wall leads to axial stress, generated by cyclic tethering of adjacent, more compliant wall segments. Axial stress then induces and augments processes necessary for aneurysm growth such as inflammation and vascular wall remodeling, as will be shown in further detail in the examples below.

Figure 3:
FIG. 3 is a schematic depiction of the walls of a normal (healthy) aorta during diastole, in which the walls are in an unexpanded state.
Figure 4:
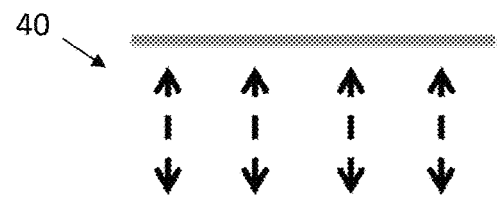
FIG. 4 is a schematic depiction of the walls of the normal (health) aorta of FIG. 3 during systole, in which the walls are in an expanded state.
Figure 5A:
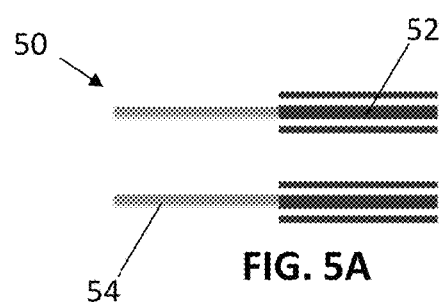
FIG. 5A is a schematic depiction of the walls of a segmentally stiff aorta during diastole.
Figure 5B:
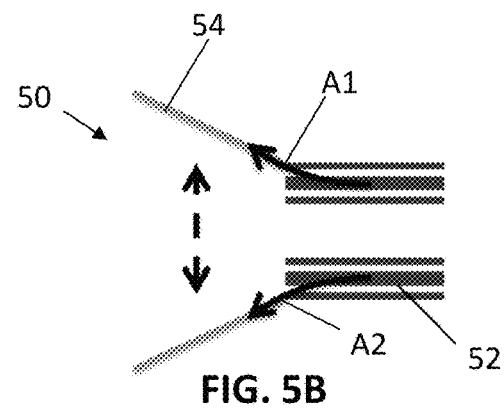
FIG. 5B is a schematic depiction of the walls of the segmentally stiff aorta during systole.

FIGS. 3-5B depict the concept of segmental aortic stiffness generating axial wall stress during systolic aortic expansion. More specifically, FIGS. 3 and 4 depict a healthy aorta 40 that is homogenously expandable, while FIGS. 5A and 5B depict a segmentally stiff aorta 50. In FIG. 3, the aorta 40 is shown in its unexpanded state during diastole, while FIG. 4 depicts the aorta 40 in systole when the aorta 40 is in its expanded state. Note that the healthy aorta 40 is homogenously expandable due to the natural compliance of the aorta 40—it has no segmental aortic stiffening. In contrast, the aorta 50 as shown in FIGS. 5A and 5B exhibits segmental aortic stiffening, with the aorta 50 having a stiff segment 52 in which the walls are relatively stiffer than the rest of the aorta 50 and a normal segment 54 having normal, compliant walls. As shown in FIG. 5A, the segmentally stiff aorta 50 in diastole has an unexpanded state that looks similar to that of a health aorta (such as the aorta 40 discussed above), with both the stiff segment 52 and the normal segment 54 having similar diameters. However, as depicted in FIG. 5B, the aorta 50 in systole has an expanded state in which the stiff segment 52 does not expand (or not as much) while the normal segment 54 does. As a result, the segmentally stiff aorta 50 is subjected to cyclical, axially tethering forces as depicted by arrows A1, A2 during the repeated circumferential expansion of the compliant wall segments of the normal segment 54 adjacent to the stiff segment 52 during systole. These tethering forces cause axial stress, which results in inflammation and vascular wall remodeling of the aortic wall, thereby ultimately causing the grown of an aneurysm. In other words, the existence of a stiff aortic segment adjacent to a more compliant aorta generates axial wall stress due to non-uniform systolic wall deformations, thereby modulating early aneurysm pathobiology.

The interventional mechanical stiffening of an aneurysm-adjacent aortic segment as disclosed in the various embodiments herein—including the stent, adhesive, and gel embodiments discuss above—limits AAA remodeling and expansion.

Below are examples of specific embodiments relating to the interventional mechanical stiffening of an aneurysm-adjacent aortic segment. They are provided for illustrative purposes only, and are not intended to limited the scope of the various embodiments in any way.

EXAMPLE

As discussed above, AAA formation is due at least in part to active, dynamic remodeling. Mechanical wall stress was an intriguing candidate for being an early trigger for remodeling. That is, biomechanical stress (i.e., shear stress, circumferential or axial wall stress) may drive adaptive arterial remodeling in response to altered hemodynamics, but also may induce inflammation and ECM remodeling, as well as VSMC apoptosis in vascular disease.

AAA growth is accompanied by increasing wall stress. While wall stress due to the vessel's expanding geometry significantly contributes to eventual rupture of the "mature" AAA, it might appear that wall stress would be unrelated to the pathophysiology in early, pre-aneurysmal stages, when aortic size has not yet overtly changed. However, enhanced wall stress may still occur due to early aortic biomechanical alterations (i.e., aortic stiffening).

A porcine pancreatic elastase ("PPE") infusion model was created. More specifically, the PPE infusion model to induce AAA in 10-week-old male C57BL/6J mice was performed as described in Azuma J, Asagami T, Dalman R, Tsao P, "Creation of murine experimental abdominal aortic aneurysms with elastase," J Vis Exp. 2009; 29:1280. In brief: after placing temporary ligatures around the proximal and distal aorta, an aortotomy was created at the bifurcation and an insertion catheter was used to perfuse the aorta for 5 minutes with saline containing porcine pancreatic elastase (1.5 U/mL; Sigma Aldrich).

The PPE-adjacent aortic segments were treated with glue. More specifically, in order to locally enhance aortic mechanical stiffness, a surgical adhesive (BioGlue, CryoLife, Atlanta) was applied to the segments adjacent to the PPE-treated aorta directly after completion of the PPE-treatment. Complete polymerization of the two-component glue (albumin/glutaraldehyde) occurred within seconds. As shown in FIG. 14B, care was taken to avoid the PPE-treated segment. For sham-treatment groups only one component of BioGlue was applied.

Mouse ultrasound studies were performed. More specifically, systolic diameter ($D_s$) and diastolic diameter ($D_d$) were quantified in the PPE-treated segment as well as in the adjacent untreated segments using M-Mode ultrasound. Circumferential cyclic strain c was calculated as $\varepsilon=(D_s-D_d)/D_d \times 100\%$. Segmental aortic stiffness (SAS) was defined as a relative index to quantify the stiffness of the PPE-treated segment in relation to the adjacent aorta, calculated as $SAS=\varepsilon_{adjacent\ aorta}/\varepsilon_{PPEsegment}$. The strain values for adjacent aorta ($\varepsilon_{adjacent\ aorta}$) represent an average strain calculated from the adjacent segments proximal and distal to the PPE-treated segment. For shear stress calculations, blood flow was assessed as previously described in Hong G, Lee J, Robinson J, Raaz U, Xie L, Huang N, Cooke J, Dai H., "Multifunctional in vivo vascular imaging using near-infrared II fluorescence," Nat Med. 2012; 18:1841-6.

Human ultrasound studies were also performed. Nineteen male volunteers of different ages (youngest age: 36, oldest age: 71, mean age: 51.9 years) were included in the study. Exclusion criteria were cardiovascular diseases (in particular AAA), diabetes and history of smoking. M-mode images tracking the anterior and posterior aortic wall motion were recorded at predefined locations (suprarenal, mid-infrarenal and proximal to the aortic bifurcation).

Systolic diameter ($D_s$) and diastolic diameter ($D_d$) were quantified in the suprarenal, mid-infrarenal and bifurcational segment of the abdominal aorta to calculate cyclic strain and SAS.

Finite element analyses of the mouse aorta were performed using the commercial finite element software package ABAQUS. The artery was modeled as a 2.0 mm long axisymmetric tube with outer diameter $D_a=0.9$ mm and arterial wall thickness $t=0.075$ mm. The intima, media, and adventitia were summarized in a single homogeneous layer modeled using an isotropic Neo-Hookean strain energy function with a shear modulus of 300 kPa. Stiffness of the stiff segment (I=1.0 mm) was modified as indicated.

An RNA quantification was also performed. Total aortic RNA was isolated and processed for qRT-PCR using standard protocols and methods.

Laser capture microdissection ("LCM") was performed as previously described in Sho E, Sho M, Nanjo H, Kawamura K, Masuda H, Dalman R L, "Comparison of celltype-specific vs. transmural aortic gene expression in experimental aneurysms," J Vasc Surg. 2005; 41:844-52. F4/80-stained macrophages were micro-dissected from frozen aortic cross sections (7 μm) using a PALM MicroBeam System (Zeiss). RNA was subsequently processed for qRT-PCR using the Single Cell-to-CT Kit (Ambion).

Standard protocols for histology, immunofluorescence, in situ DHE staining, and in situ hybridization were used.

Ex vivo aortic mechanical stimulation was performed. More specifically, abdominal aortae were explanted, cannulated and mounted in the heated vessel chamber of a pressure arteriograph system (Model 110P, Danish Myotechnology, Copenhagen, Denmark) and stretched to in vivo length. The aorta was then subjected to an automated pressure protocol, cyclically alternating between 80 mmHg and 120 mmHg with a frequency of 4/minute for one hour. To stiffen/restrain either the complete aorta or just the central segment (to simulate segmental stiffening), a silicone cuff (SILASTIC Laboratory Tubing, inner diameter: 0.51 mm; Dow Corning) was placed around the aorta as shown in FIG. 9. After conclusion of the experiment, the aorta was removed from the cannulas and processed for RNA isolation.

With respect to the statistical information and analysis provided herein, data are presented herein as mean±SEM. For comparison of 2 groups, a Mann-Whitney test was performed; for multiple groups (≥3 groups), comparison was accomplished by a Kruskal-Wallis test with Dunn's posttest. Ultrasound data comparing 2 groups/treatments over time were analyzed by a permutation F-test based on 2-way repeated measures ANOVA. For each treatment assignment, a repeated measures ANOVA was performed and a null distribution of the p-value was derived for treatment effect. The p-value from the permutation test was then established as the percentage of the null p-values less than the p-value from the real data. To compare ultrasound parameters within one treatment group over time, the Friedman's test was used. For correlation analysis of animal ultrasound data, the Spearman correlation was used. For correlation analyses of human ultrasound data, the Pearson correlation was used after passing D'Agostino-Pearson omnibus normality test. A value of p≤0.05 (two-sided) was considered statistically significant.

All animal protocols were approved by the Administrative Panel on Laboratory Animal Care at Stanford University (labanimals.stanford.edu/) and followed the National Institutes of Health and USDA Guide lines for Care and Use of Animals in Research.

Results

Based on the results, it can be concluded that aortic stiffening precedes aneurysmal dilation in experimental AAA.

Figure 6A:
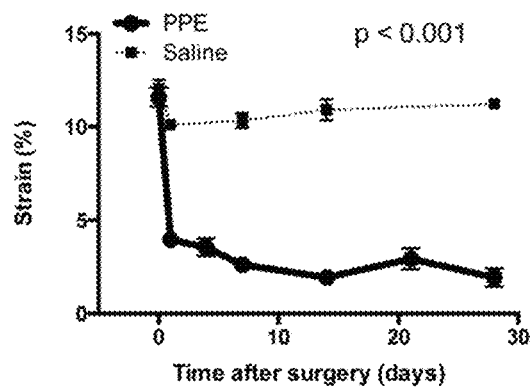
FIG. 6A is a line graph depicting temporal development of circumferential cyclic strain of PPE-treated and saline-treated segments.
Figure 6B:
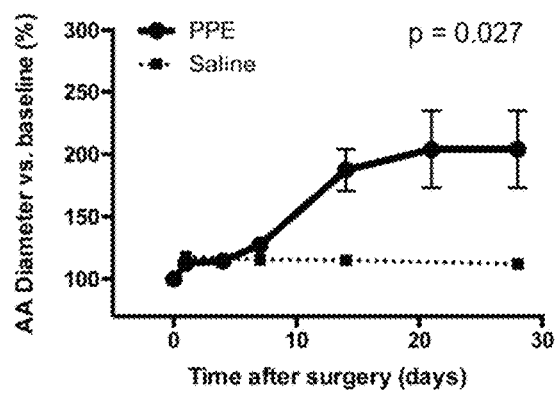
FIG. 6B is a line graph depicting diameter development of the PPE-treated and saline-treated segments (% vs. baseline (d0)) over time.

The temporal relationship between aortic biomechanical alterations and aneurysmal dilation in the porcine pancreatic elastase (PPE)-infusion model of murine AAA was investigated. As shown in FIGS. 6A and 6B, circumferential cyclic aortic strain (as a measure of vascular stiffness) and aortic diameter were monitored over time in the PPE-treated segment and saline-perfused controls via M-Mode ultrasound.

With reference to FIG. 6A, while native abdominal aortae exhibited a baseline cyclic strain of about 12%, PPE-infusion rapidly induced a substantial strain reduction of more than 50% in the treated segment at d1 followed by further declines until d14, after which it remained stable until d28. In contrast, saline infusion only resulted in a minor strain reduction in the corresponding segment.

As shown in FIG. 6B, the aortic diameter, however, displayed insignificant enlargement up to d7 post-PPE and post-saline. The PPE-treated segment then dilated markedly between d7 and d14. Afterwards the aortic diameter remained relatively stable up to d28.

Figure 6C:
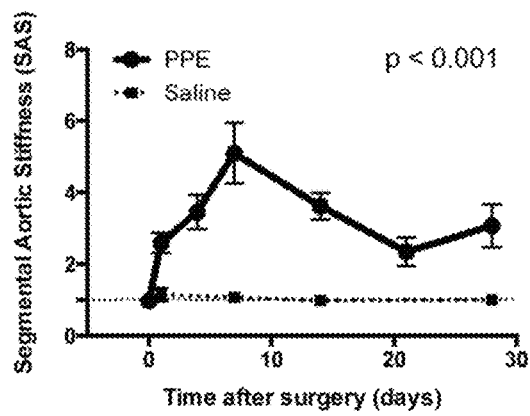
FIG. 6C is a line graph depicting temporal analysis of segmental aortic stiffness ("SAS") of the PPE-treated or saline-treated segment relative to the adjacent abdominal aorta.
Figure 6D:
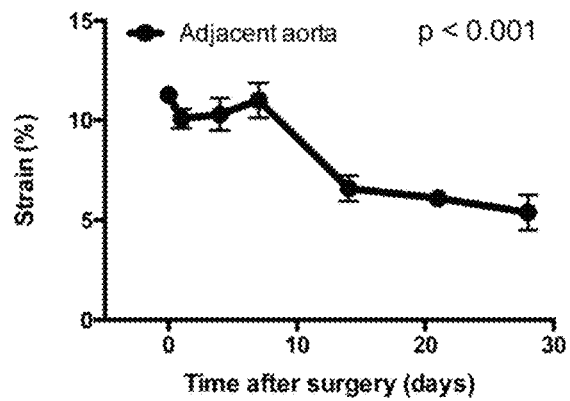
FIG. 6D is a line graph depicting temporal analysis of the circumferential cyclic strain of the aorta adjacent to the PPE-treated segment.
Figure 6E:
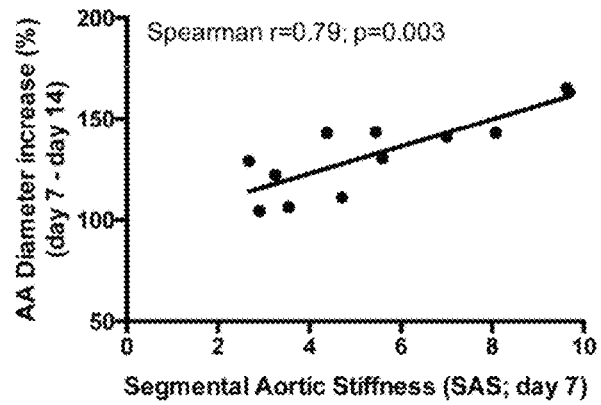
FIG. 6E is a scatter plot graph depicting the correlation between the segmental aortic stiffness ("SAS") at day 7 and the consecutive diameter increase of the PPE-treated segment in the following 7 days.
Figure 6F:
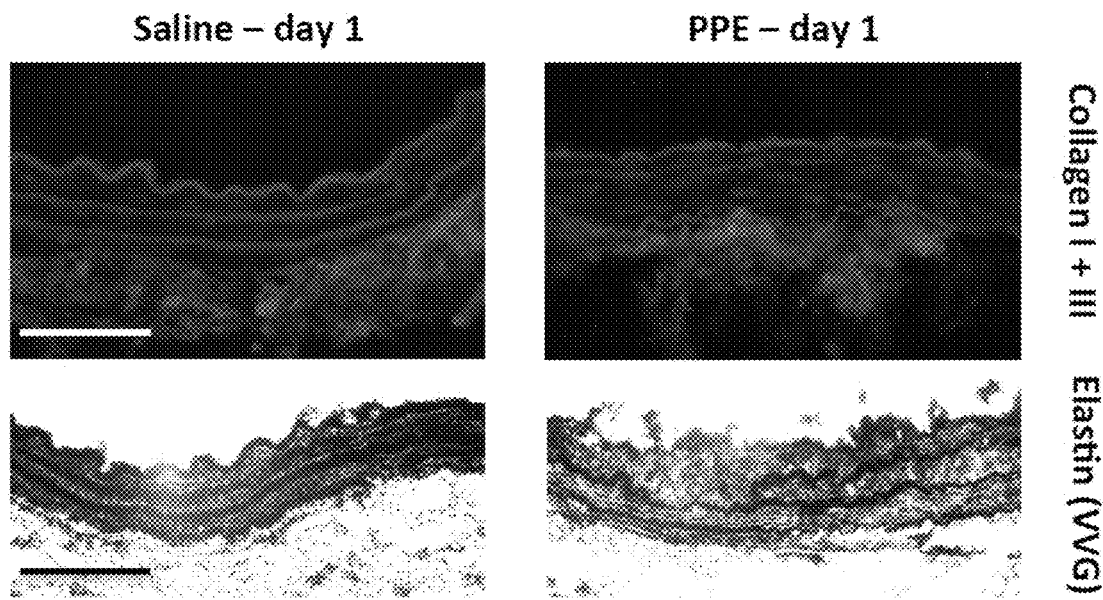
FIG. 6F is a set of images depicting representative immunofluorescence staining for collagen I+III (red) with green autofluorescence of elastin lamellae in the upper two panels and Modified Elastin Verhoeff's Van Gieson ("VVG") staining in the lower two panels.

As evidenced by FIG. 6F, investigating possible mechanisms for the rapid stiffening of the PPE-treated segments we found remarkable elastin fragmentation, while pro-fibrotic responses were only moderate.

With respect to FIGS. 6A-6F, data are mean±SEM, and n=5-13 for each condition/time point. Further, p values denote differences between PPE and saline groups by permutation F-test for FIGS. 6A-6C, aortic strain differences in PPE treated animals over time by Friedman's test for FIG. 6D, and significance level of Spearman correlation for FIG. 6E.

The results show that segmental aortic stiffening generates axial wall stress in the AAA-prone segment. Having identified rapid early mechanical stiffening of the aneurysm-prone segment (i.e. reduced cyclic strain), the role of that stiffening in aneurysm development was investigated. It was hypothesized that segmental aortic stiffening (SAS; defined as enhanced stiffness of the aneurysm-prone segment relative to the adjacent aorta) would generate adverse wall stress during cyclic deformation of the aortic wall, eventually resulting in AAA formation. Thus, in silico wall stress analysis employing a finite element model was performed.

Figure 7A:
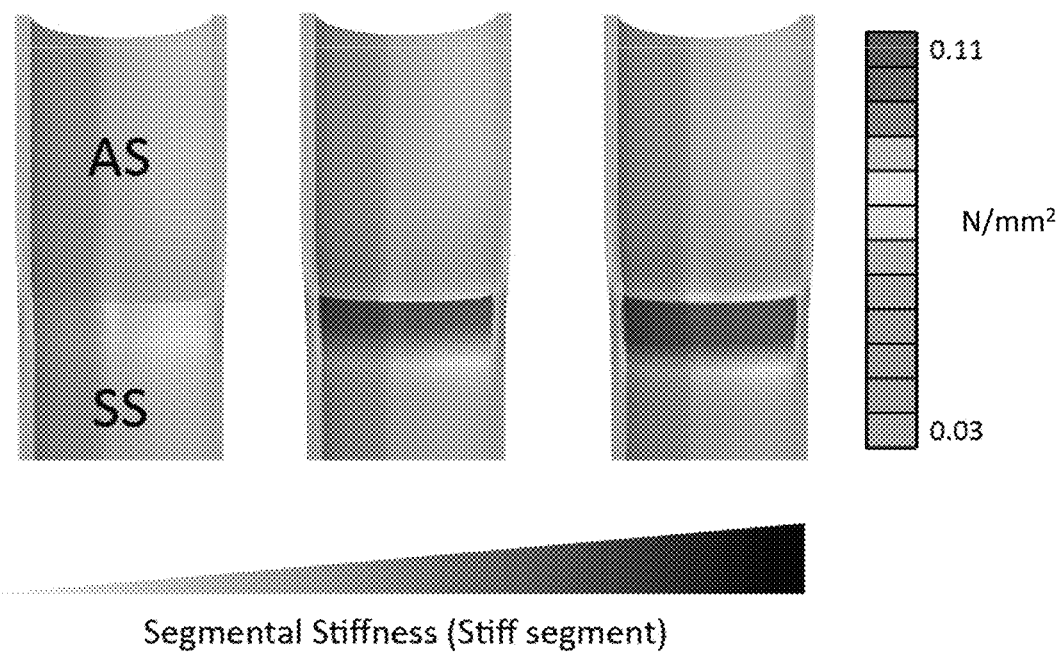
FIG. 7A is a schematic depiction of a finite elements model ("FEA") showing axial stress analysis of segmental aortic stiffening in Newtons per square millimeter ($N/mm^2$) in which the stiffness of the stiff aortic segment was increased (shear moduli: 500 kPa left vessel, 1100 kPa middle vessel, 1700 kPa right vessel) to demonstrate the impact of segmental stiffness on axial stress generation.
Figure 7B:
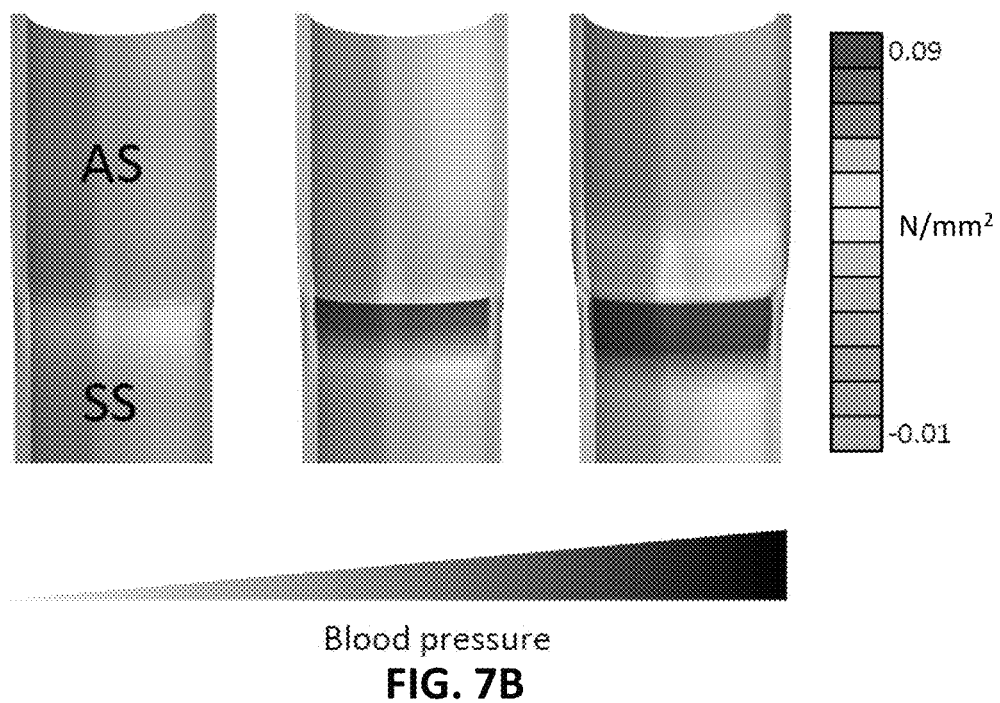
FIG. 7B is a schematic depiction of a finite elements model ("FEA") showing axial stress analysis of segmental aortic stiffening in $N/mm^2$ in which the intraluminal pressure was increased (left vessel: 80 mmHg, middle vessel: 130 mmHg, right vessel: 180 mmHg) to visualize the influence of blood pressure on axial stresses in a segmentally stiff aorta.
Figure 7C:
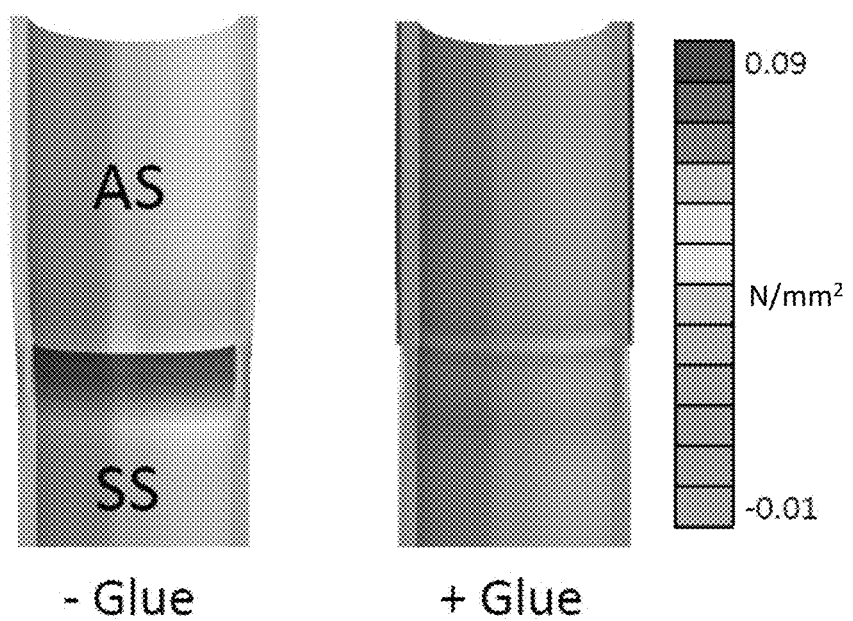
FIG. 7C is a schematic depiction of a finite elements model ("FEA") showing axial stress analysis of segmental aortic stiffening in $N/mm^2$ in which a segmentally stiff aorta without external stiffening (left) is compared to a segmentally stiff aorta that is subjected to external stiffening of the adjacent compliant segments (simulating glue treatment; right) to demonstrate axial stress reduction and homogenization induced by the interventional external stiffening.

Using a simplified approach, the infrarenal mouse aorta was modeled as a cylindrical tube in a finite elements model ("FEA")-based axial stress analysis of segmental aortic stiffening in which the aorta was subjected to various mechanical conditions and resulting axial (longitudinal) stress (N/mm$^2$) was depicted as shown in FIGS. 7A-7C. More specifically, to examine the effects of segmental stiffening, a pressure of 130 mmHg (approximating systolic blood pressure) was simulated and a segment of increasing stiffness (SS) was introduced adjacent to a non-stiff segment (AS). As shown in FIG. 7A, it was found that increasing segmental stiffness progressively induced axial stress in the stiff segment extending from the segmental interface.

As hypertension represents a risk factor for AAA, we explored the impact of high blood pressure levels on axial wall stress by pressurizing our FEA model with a fixed stiffness of the stiff segment up to 180 mmHg. As shown in FIG. 7B, this simulation revealed that high blood pressure augmented segmental stiffness-based wall stresses.

Taken together these data suggest that segmental aortic stiffness generates substantial axial wall stresses that also are susceptible to a hypertensive environment.

It was also shown that segmental aortic stiffness correlates with experimental aneurysm progression. To further investigate the significance of segmental aortic stiffening (SAS) as an inducer of aneurysm growth, a temporal analysis of SAS was performed in vivo and correlated to aneurysm growth in the PPE model. As shown in FIGS. 6C and 6D, a continuous increase in SAS after aneurysm-induction was found, peaking at d7, which was due to increasing stiffness of the PPE-treated segment (5-fold higher than adjacent aorta). Of note, the SAS peak coincided with the onset of aneurysm expansion. Moreover, as shown in FIG. 6E, the magnitude of SAS at d7 correlated with subsequent aortic enlargement between d7 and d14.

As shown in FIGS. 6C and 6D, after d7, SAS declined as a result of progressive stiffening of the adjacent aortic segments, which was accompanied by decelerating aortic diameter enlargement, as best shown in FIG. 6B. As evidenced by FIG. 6C, saline-infused controls did not exhibit significantly enhanced SAS at any point during the entire observation period.

Pro-fibrotic mechanisms accompany stiffening of AAA-adjacent segments, thereby reducing segmental aortic stiffness.

Having detected decreased SAS at d14 due to stiffening in the AAA-adjacent aorta, the underlying molecular mechanisms were investigated. FIGS. 8A-8D examine the stiffening mechanisms of AAA-adjacent aorta. FIG. 8A depicts temporal analysis of the Col1a1 and Col3a1 gene expression in the AAA-adjacent aorta compared to the AAA (PPE-treated) segment. FIG. 8B depicts temporal analysis of miR-29b expression in the AAA-adjacent aorta compared to the AAA (PPE-treated) segment. FIG. 8C depicts in situ hybridization for miR-29b (purple-blue dye) and red nuclear counterstain in the AAA-adjacent aortic segments (original magnification 400×, scale bar 50 μm). FIG. 8D depicts representative images of the aortic wall taken from AAA-adjacent aortic segments 7 days or 14 days after PPE-treatment stained with Picrosirius Red (upper panels; red: collagen; yellow: muscle) and Elastin VVG staining (lower panels) (original magnification 400×, scale bar 50 μm). In these figures, n=5 for each time point, and p values denote differences between expression levels by Kruskal-Wallis test with Dunn's posttest.

As shown in FIG. 8D, medial collagen deposition—a known determinant of arterial stiffness—was remarkably enhanced in AAA-adjacent segments at d14 after aneurysm induction (compared to d7). Further, as shown in FIG. 8A, expression of the collagen genes Col1a1 and Col3a1 was increased in the adjacent segments compared to the AAA segment itself at d7, preceding the histological alterations. In line with this observation, as shown in FIG. 8B, miR29b—previously shown to be an epigenetic negative regulator of collagen expression in AAA—was similarly downregulated at d7. More specifically, in situ hybridization (ISH) indicated marked miR-29b downregulation within the aortic media, as shown in FIG. 8C.

In contrast to the marked pro-fibrotic changes, as shown in FIG. 8D, elastin architecture appeared unaffected in the AAA-adjacent aorta.

Figure 9A:
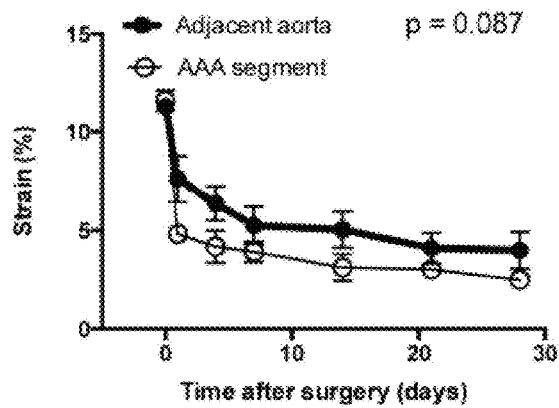
FIG. 9A is a line graph depicting temporal analysis of the circumferential cyclic strain of the glue-treated adjacent aorta (bold line) in relation to the PPE-treated segment (thin line).

It was also shown that interventional reduction of segmental stiffness reduces wall stress and aneurysm progression. To investigate the potential causative role of segmental aortic stiffening as a mechanism driving AAA development, the adjacent aorta next to the PPE-treated segment was focally stiffened by peri-aortic application of BioGlue, a surgical adhesive with a relatively high material stiffness, as shown in FIGS. 14A and 14B. More specifically, FIG. 14A depicts the abdominal aorta before glue application, while FIG. 14B depicts the aorta after glue application to the segments adjacent to the PPE-treated segment. Please note that the scale bar in the figures represents 1 mm. As shown in FIG. 9A, glue application induced rapid and sustained stiffening of the adjacent aortic segments, resulting in nearequalization of stiffness between the PPE-treated segment and the glue-treated adjacent segments. This was reflected in a significant reduction of SAS compared to sham-glue treated controls, as shown in FIG. 9B.

Figure 9B:
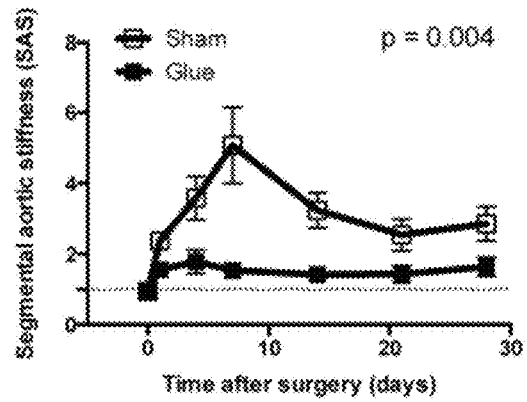
FIG. 9B is a line graph depicting temporal analysis of segmental aortic stiffness ("SAS") in glue-treated aortas compared to sham-glue-treated conditions.
Figure 9C:
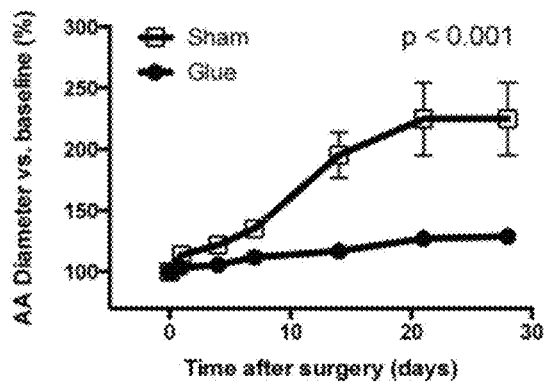
FIG. 9C is a line graph depicting diameter development of the PPE-treated segment in glue-treated vs. sham-glue-treated conditions.
Figure 9D:
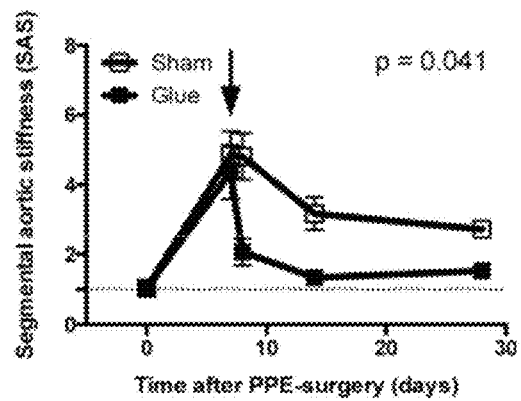
FIG. 9D is a line graph depicting temporal development of SAS following delayed glue or sham treatment 7 days (as identified by the arrow) after PPE surgery.
Figure 9E:
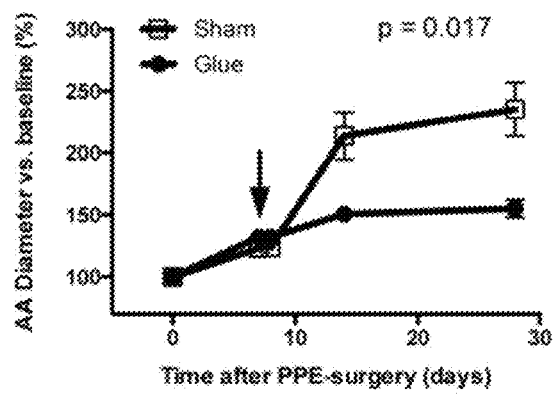
FIG. 9E is a line graph depicting temporal development of aortic diameter following delayed glue or sham treatment 7 days (as identified by the arrow) after PPE surgery.
Figure 9F:
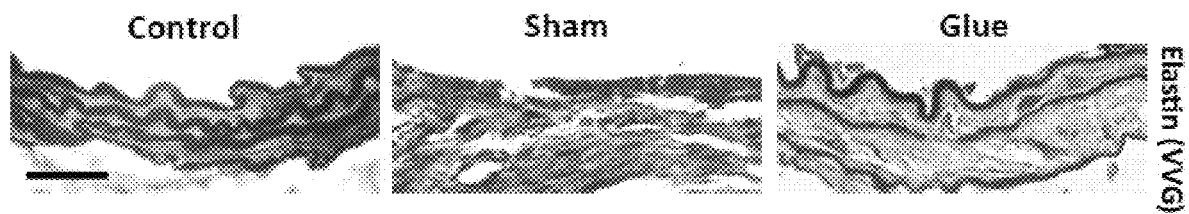
FIG. 9F is a set of images depicting representative Elastin VVG staining of the aortic wall taken from native abdominal aortas (control) or PPE-treated segments at day 14 after additional treatment of the adjacent aorta with glue or sham-glue (original magnification 400×; scale bars 50 μm).
Figure 9G:
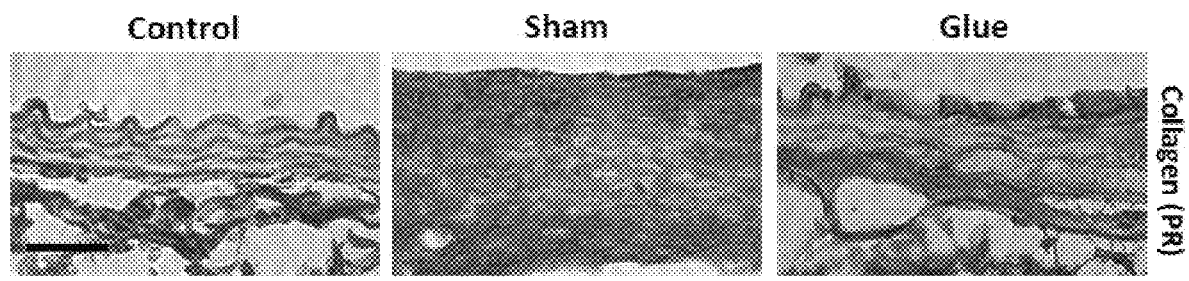
FIG. 9G is a set of images depicting representative Picrosirius Red staining of the aortic wall taken from native abdominal aortas (control) or PPE-treated segments at day 14 after additional treatment of the adjacent aorta with glue or sham-glue (original magnification 400×; scale bars 50 μm).

FIGS. 9A-9G depict the effects of glue-treatment on segmental aortic stiffness and aneurysm progression. FIG. 9A depicts temporal analysis of the circumferential cyclic strain of the glue-treated adjacent aorta (bold line) in relation to the PPE-treated segment (thin line). FIG. 9B depicts temporal analysis of segmental aortic stiffness ("SAS") in glue-treated aortas compared to sham-glue-treated conditions. FIG. 9C depicts diameter development of the PPE-treated segment in glue-treated vs. sham-glue-treated conditions. FIG. 9D depicts temporal development of SAS following delayed glue or sham treatment 7 days after PPE surgery (see arrow). FIG. 9E depicts temporal development of aortic diameter following delayed glue or sham treatment 7 days after PPE surgery (see arrow). FIG. 9F depicts representative Elastin VVG staining of the aortic wall taken from native abdominal aortas (control) or PPE-treated segments (d14) after additional treatment of the adjacent aorta with glue or sham-glue (original magnification 400×; scale bars 50 µm). FIG. 9G depicts representative Picrosirius Red staining of the aortic wall taken from native abdominal aortas (control) or PPE-treated segments (d14) after additional treatment of the adjacent aorta with glue or sham-glue (original magnification 400×; scale bars 50 µm). Please note that EVG staining was used to depict the integrity of the medial elastin lamellae. Picrosirius Red staining aided the visualization of the aortic wall architecture and collagen remodeling. In these figures, n=7 for each time point; p values denote differences between aortic segments in FIG. 9A and treatment groups in FIGS. 9B-9E by permutation F-test.

Figure 15:
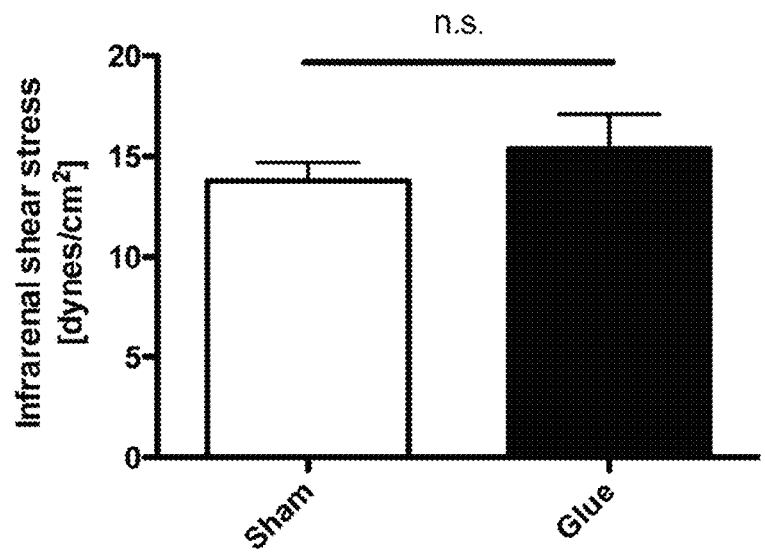
FIG. 15 is a bar graph depicting shear stress occurring in the PPE-treated segment as captured by ultrasound measurements on day 7 after PPE-induction.
Figure 16:
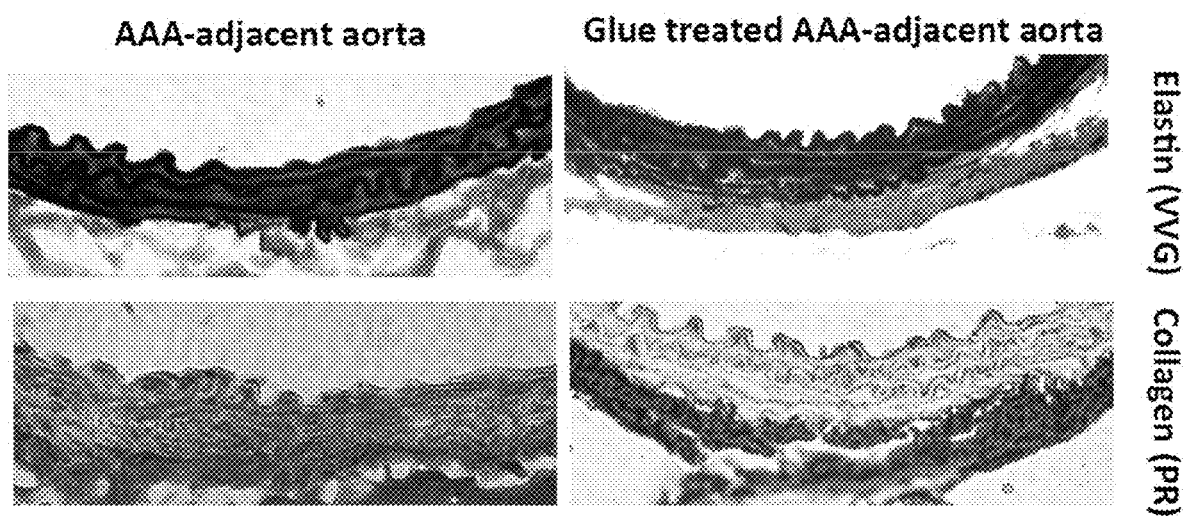
FIG. 16 is a set of images depicting elastin architecture via Verhoef Van Gieson staining in the upper panels and collagen deposition via Picrosirius Red staining in the lower panels of the AAA-adjacent aorta on day 14 with glue treatment in the right panels and without glue treatment in the left panels.

To exclude the possibility that aortic constriction due to segmental glue treatment might lead to alterations of the downstream aortic flow and fluid shear stress, thereby affecting aneurysm formation, the aortic diameter of the glue-treated segment and the downstream flow profile were monitored. Neither luminal narrowing (data not shown) nor elevated flow shear stress levels were detected, as shown in FIG. 15, which depicts shear stress occurring in the PPE-treated segment via ultrasound measurements for shear stress calculation that were taken at day 7 after PPE-induction. Further, as shown in FIG. 16, glue treatment of the adjacent aorta did not cause perturbations of its elastin architecture nor an enhanced fibrotic response, suggesting that direct mechanical interaction with the aortic wall caused the stiffening effect. More specifically, FIG. 16 depicts elastin architecture (Verhoef Van Gieson staining, shown in the upper panels) and collagen deposition (Picrosirius Red staining, shown in the lower panels) of the AAA-adjacent aorta (day 14) with glue treatment as shown in the right panels) and without glue treatment as shown in the left panels. As shown in the figure, while the elastin architecture of the aortic wall is unaffected by surrounding glue treatment, collagen deposition is reduced (possibly reflecting an effect of mechanical offloading of the glue-stiffened aorta).

Further, as shown in FIG. 7C, our finite element model demonstrated that stiffness equalization between all segments (i.e., reduction of SAS) resulted in decreased and homogenized axial stress. As discussed above, FIG. 7C depicts a segmentally stiff aorta that is initially depicted on the left when it has not been subjected to external stiffening and also is depicted on the right after it has been subjected to external stiffening of the adjacent compliant segments (simulating glue treatment) to demonstrate axial stress reduction and homogenization induced by the intervention.

Finally, comparing aortic diameter between glue-treated and sham glue-treated animals, with reference to FIG. 9C, it was found that PPE-induced aortic expansion was significantly reduced when adjacent segments were immobilized by glue application. The figure shows that the expected rapid diameter increase between d7 and d14 was suppressed by the glue treatment.

To further test the efficiency of delayed glue treatment on aneurysm progression, additional experiments were performed with glue intervention at d7 post PPE, when there already is a small dilation combined with a high segmental stiffness, as shown in FIGS. 9D and 9E. As a result, it was found that delayed glue-stiffening of the AAA-adjacent aorta also significantly reduces SAS and thereby represses the consecutive aneurysmal diameter progression compared to sham-glue treated animals.

The results also show that a reduction of segmental stiffness modulates critical features of AAA pathobiology. Since AAA formation is accompanied by extensive extracellular matrix (ECM) remodeling, histologic analyses of the aneurysm wall was performed, focusing on elastin and collagen architecture. As shown in FIG. 9F, extensive destruction of elastin fibers—a hallmark of aneurysm pathology—was present in sham-glue-treated mice on d14 after PPE infusion. Further, it is shown in FIG. 9G that Picrosirius Red staining revealed disturbed wall architecture with general wall thickening, loss of layered structure, and diffuse collagen enrichment. In contrast, elastin structure and wall layering were better preserved in the glue-treated group while collagen accumulation appeared less prominent.

AAA pathology includes enhanced reactive oxygen species (ROS) generation, vascular inflammation, vascular smooth muscle cell (VSMC) apoptosis and enhanced MMP activity. To assess the impact of SAS-modulations on these endpoints, the PPE-treated aorta was analyzed at d7, which marks the peak of segmental stiffening but precedes the prominent diameter increase between d7 and d14.

Figure 10A:
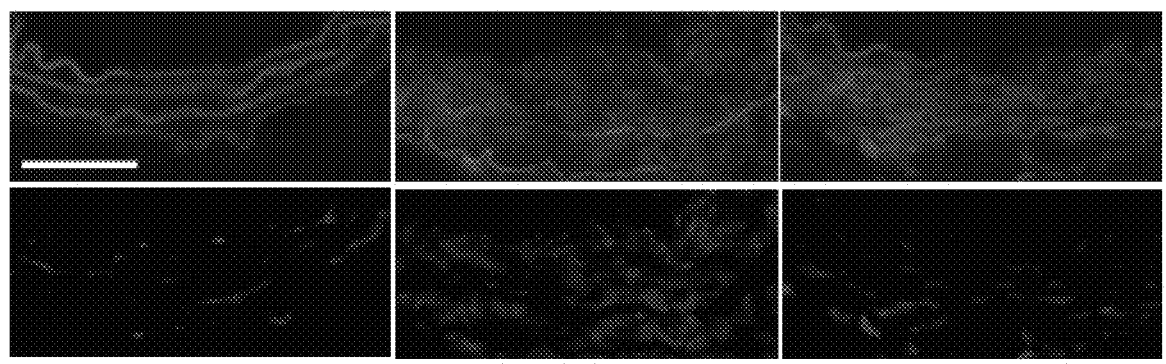
FIG. 10A is a set of images depicting in situ DHE staining of native abdominal aortas (control) or PPE-treated segments after additional treatment of the adjacent aorta with glue or sham-glue at day 7.
Figure 10B:
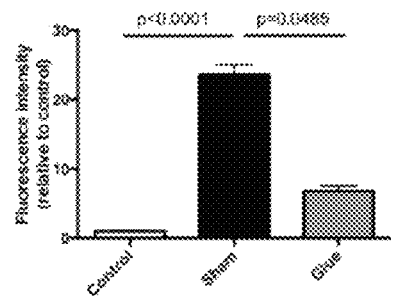
FIG. 10B is a bar graph depicting average fluorescence from three high power fields of three different aortas per group (control, sham, and glue).
Figure 10C:
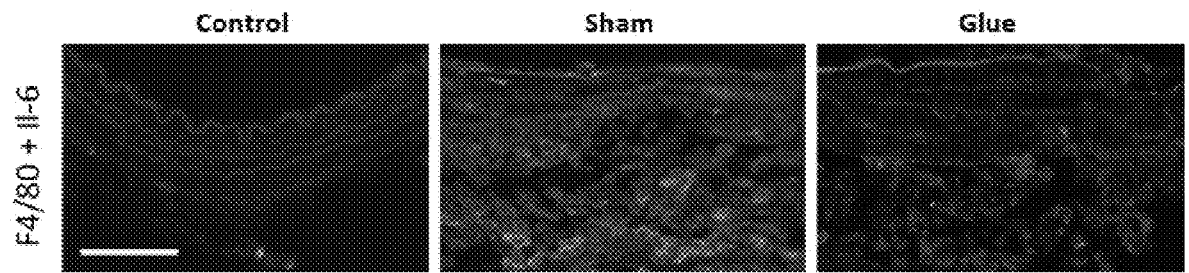
FIG. 10C is a set of images depicting representative co-staining of macrophages (red F4/80 marker) and the green labeled cytokine IL-6 in native abdominal aortas (control) or PPE-infused segments at day 7 after additional treatment of the adjacent aorta with glue or sham-glue (original magnification 400×, scale bar 50 μm).
Figure 10D:
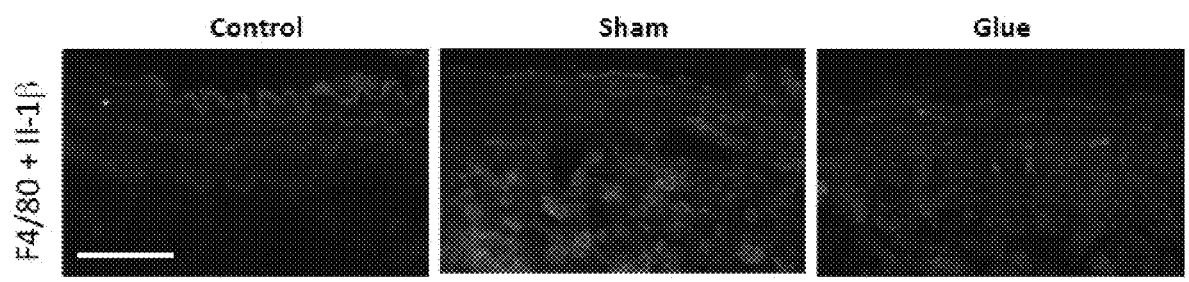
FIG. 10D is a set of images depicting representative co-staining of macrophages (red F4/80 marker) and the green labeled cytokine IL-1β in native abdominal aortas (control) or PPE-infused segments at day 7 after additional treatment of the adjacent aorta with glue or sham-glue (original magnification 400×, scale bar 50 μm).
Figure 10E:
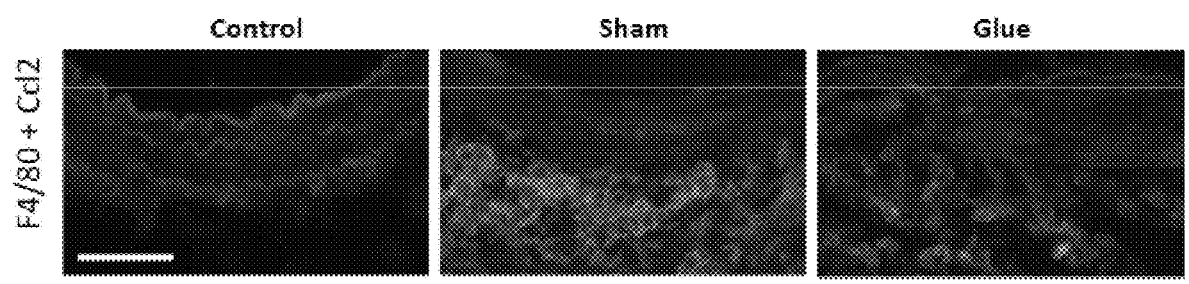
FIG. 10E is a set of images depicting representative co-staining of macrophages (red F4/80 marker) and the green labeled cytokine Ccl2 in native abdominal aortas (control) or PPE-infused segments at day 7 after additional treatment of the adjacent aorta with glue or sham-glue (original magnification 400×, scale bar 50 μm).
Figure 10F:
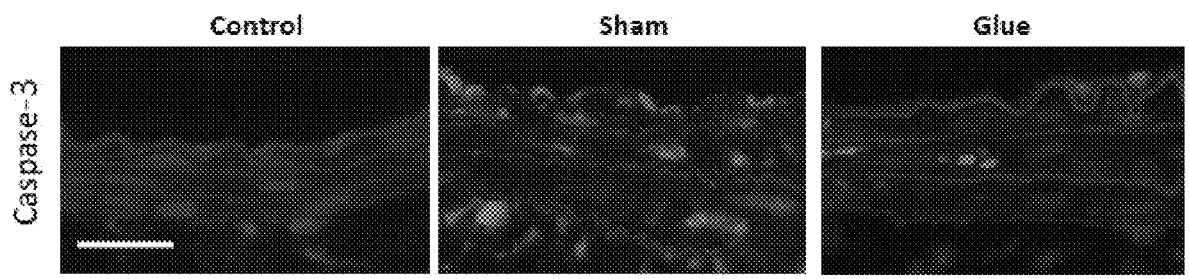
FIG. 10F is a set of images depicting corresponding immunostaining of activated caspase-3 (red).
Figure 10G:
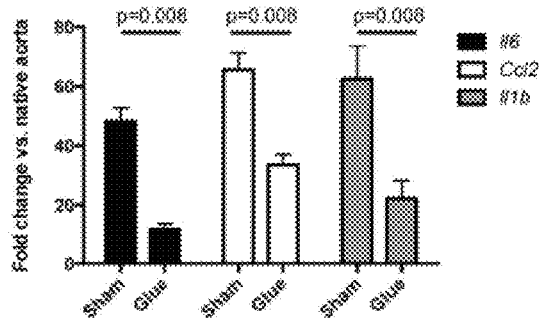
FIG. 10G is a bar graph depicting expression of Il6, Ccl2, and Il1b in the PPE-infused segment at day 7 after additional glue or sham-glue treatment of the adjacent aorta, quantified in whole tissue.
Figure 10H:
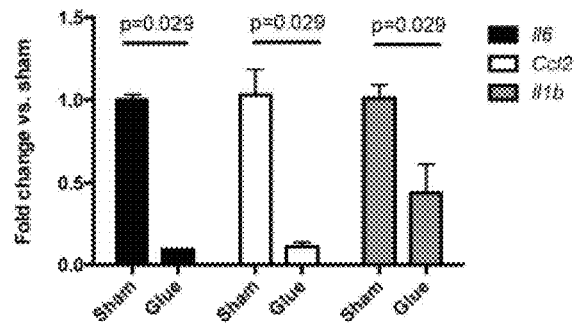
FIG. 10H is a bar graph depicting expression of Il6, Cc/2, and Il1b in the PPE-infused segment at day 7 after additional glue or sham-glue treatment of the adjacent aorta, quantified in laser-captured macrophages.
Figure 10I:
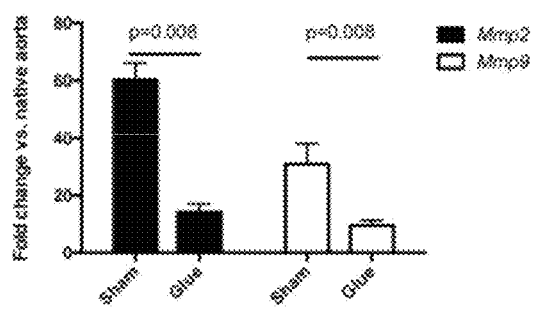
FIG. 10I is a bar graph depicting expression analysis of Mmp2 and Mmp9 in the PPE-infused segment at day 7 after additional glue or sham-glue treatment of the adjacent aorta.
Figure 10J:
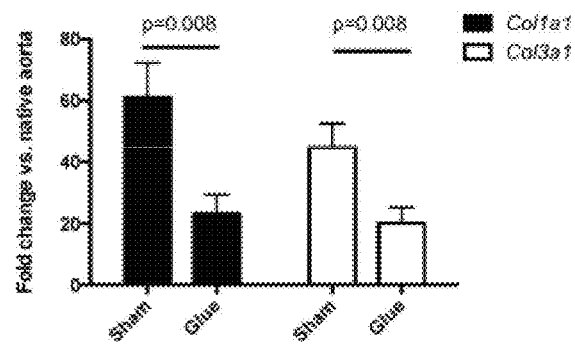
FIG. 10J is a bar graph depicting expression analysis of Col1a1 and Col3a1 in the PPE-infused segment at day 7 after additional glue or sham-glue treatment of the adjacent aorta.

In situ dihydroethidium (DHE) fluorescence was performed to monitor ROS generation. FIGS. 10A-10J depict the effects of glue-induced aortic stiffening on ROS generation and parameters of inflammation, apoptosis and ECM remodeling. More specifically, FIG. 10A depicts in situ DHE staining of native abdominal aortas (control) or PPE-treated segments after additional treatment of the adjacent aorta with glue or sham-glue (d7). ROS production was indicated by red fluorescence. Autofluorescence from elastic lamellae (depicted in green in the upper row) was subtracted (bottom row). In this figure, the original magnification was ×400 and the scale bar represents 50 µm. FIG. 10B depicts quantification of average fluorescence from 3 high power fields of 3 different aortas per group. FIG. 10C depicts representative co-staining of macrophages (red F4/80 marker) and the green labeled cytokine IL-6 in native abdominal aortas (control) or PPE-infused segments (d7) after additional treatment of the adjacent aorta with glue or sham-glue (original magnification 400×, scale bar 50 µm). FIG. 10D depicts representative co-staining of macrophages (red F4/80 marker) and the green labeled cytokine IL-1β in native abdominal aortas (control) or PPE-infused segments (d7) after additional treatment of the adjacent aorta with glue or sham-glue (original magnification 400×, scale bar 50 µm). FIG. 10E depicts representative co-staining of macrophages (red F4/80 marker) and the green labeled cytokine Ccl2 in native abdominal aortas (control) or PPE-infused segments (d7) after additional treatment of the adjacent aorta with glue or sham-glue (original magnification 400×, scale bar 50 μm). Colocalization results in orange/yellow color. Nuclei are Hoechst stained (blue). FIG. 10F depicts corresponding immunostaining of activated caspase-3 (red). FIG. 10G depicts expression of Il6, Ccl2, and Il1b in the PPE-infused segment (d7) after additional glue or sham-glue treatment of the adjacent aorta, quantified in whole tissue. FIG. 10H depicts expression of Il6, Ccl2, and Il1b in the PPE-infused segment (d7) after additional glue or sham-glue treatment of the adjacent aorta, quantified in laser-captured macrophages. FIG. 10I depicts expression analysis of Mmp2 and Mmp9 (all vs. native control) in the PPE-infused segment (d7) after additional glue or sham-glue treatment of the adjacent aorta. FIG. 10J depicts expression analysis of Col1a1 and Col3a1 (all vs. native control) in the PPE-infused segment (d7) after additional glue or sham-glue treatment of the adjacent aorta. In these figures, p values denote differences between treatment groups by Kruskal Wallis test with Dunn's posttest (in FIG. 10B) or Mann-Whitney test (in FIGS. 10G-10J).

As shown in FIGS. 10A and 10B, PPE-treated segments exhibited enhanced nuclear fluorescence compared to native controls while glue treatment resulted in a significant decrease in ROS production.

Inflammation was quantified by aortic macrophage infiltration and cytokine analysis. As shown in FIGS. 10C through 10E, extensive macrophage infiltration of the aortic wall was present 7 days after aneurysm induction as assessed by immunofluorescence, accompanied by enhanced aortic gene expression of Il6, Ccl2 and Il1b (as best shown in FIG. 10G). Glue treatment reduced macrophage infiltration as well as cytokine expression, as shown in FIGS. 10O, 10D, and 10E.

Figure 17:
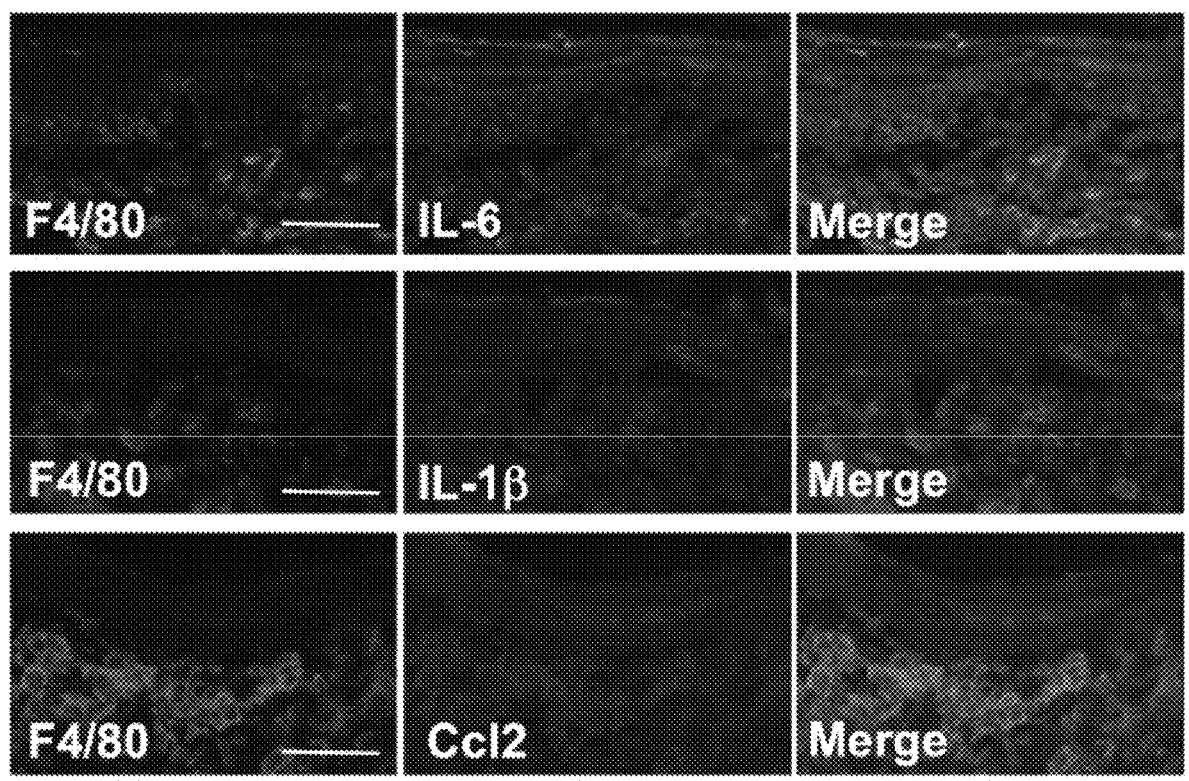
FIG. 17 is a set of images depicting immunofluorescence macrophage co-staining for inflammatory cytokines IL-6, IL-1β and Ccl2 on day 7 after PPE-treatment.

As best shown in FIG. 17, immunofluorescence additionally revealed macrophage co-localization with each of these cytokines. FIG. 17 depicts immunofluorescence macrophage co-staining for inflammatory cytokines IL-6, IL-1β and Ccl2 on day 7 after PPE-treatment. Macrophages (F4/80) are stained red (left panels), while IL-6, IL-1β and Ccl2 are shown in green (middle panels). Merged images (right panels) demonstrate macrophages co-localize with cytokines (orange). Nuclei are stained blue (Hoechst) in merged pictures.

To further delineate the role of macrophages in vascular cytokine production, gene expression profiles of macrophages directly isolated from the PPE-aneurysm sections were analyzed via laser capture microdissection ("LCM"). To this end, as shown in FIGS. 18A-18D, macrophages were micro-dissected (positive F4/80 staining) from the aortic wall and macrophage transcript enrichment was confirmed by enhanced Emr1 expression (encoding for F4/80 protein) compared to randomly captured F4/80-negative cells. Macrophages isolated from sham-glue treatment exhibited significantly higher expression of Il1b, Il6 and Ccl2 compared to those from glue-stiffened samples, as best shown in FIG. 10H.

Figure 18A:
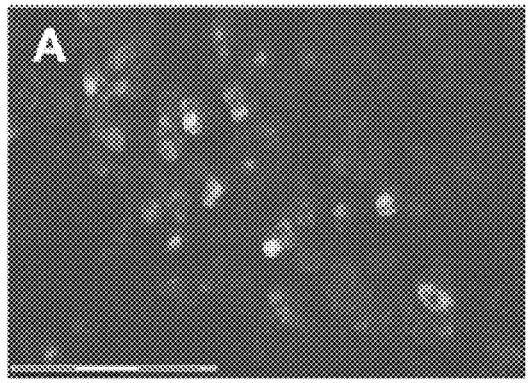
FIG. 18A is a photograph of macrophages with F4/80-fluorescent labels.
Figure 18B:
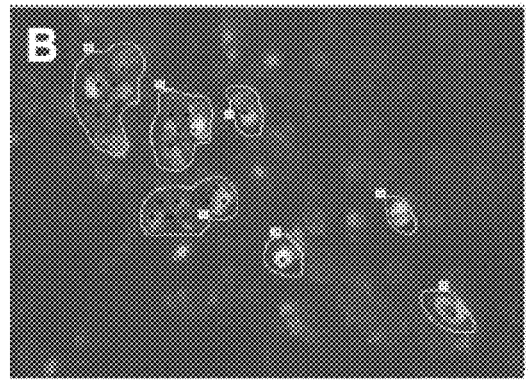
FIG. 18B is a photograph of macrophages being selectively targeted.
Figure 18C:
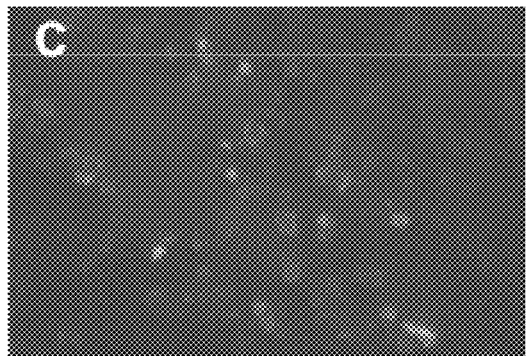
FIG. 18C is a photograph of macrophages being isolated via laser capture microdissection ("LCM").
Figure 18D:
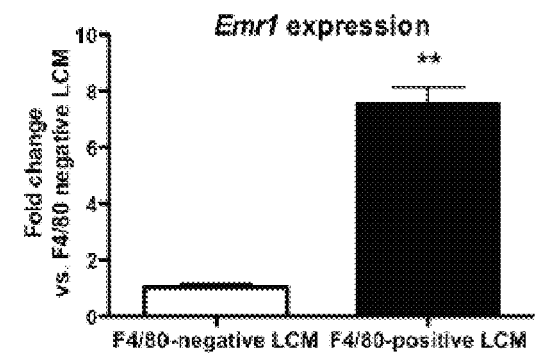
FIG. 18D is a bar graph depicting confirmation of macrophage transcript enrichment via enhanced Emr1 expression compared to LCM-isolated F4/80-negative cells.

FIGS. 18A-18D depict macrophage isolation via laser capture microdissection (LCM). More specifically, the macrophages (with F4/80-fluorescent label as shown in FIG. 18A) were selectively targeted as shown in FIG. 18B. Then the macrophages were isolated via LCM as shown in FIG. 18C. Macrophage transcript enrichment was confirmed via enhanced Emr1 expression compared to LCM-isolated F4/80-negative cells. The "**" in FIG. 18D indicates p<0.001.

Assessing apoptosis, we detected enhanced capase-3 activity in the intimal and medial layer of PPE-treated aortic wall, which was reduced in the glue-treated group, as best shown in FIG. 10F.

MMP2 and MMP9 are essential for matrix macromolecule degradation in AAA. In accordance with the substantial elastin breakdown found in PPE-treated segments, both Mmp2 and Mmp9 were significantly upregulated. Glue-stabilization of the adjacent aortic segments—which prevented extensive elastin breakdown and collagen remodeling—minimized Mmp expression, as shown in FIG. 10I. Additionally, as shown in FIG. 10J, this intervention reduced enhancement of Col1a1 and Col3a1 expression after aneurysm induction.

It was also shown that ex vivo segmental aortic stiffening induces upregulation of AAA-related genes. The mechanism of SAS was examined as a driver of AAA pathogenesis by validating our in vivo findings ex vivo. More specifically, murine abdominal aortic segments were explanted and mounted onto a pressure myograph system. Aortae were then subjected to physiologic pressure levels, cyclically alternating between 80 mmHg and 120 mmHg. To simulate aortic stiffening, the "systolic" expansion of either the entire aortic segment (complete stiffening) or just the central aortic segment (segmental stiffening) was restrained by an externally applied silicone cuff, as shown in FIGS. 11A-2, 11A-3, and 13. After one hour of cyclic pressurization, aortic gene expression was analyzed.

Figures 1, 11A:
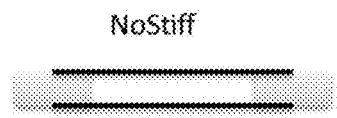
Figures 2, 11A:
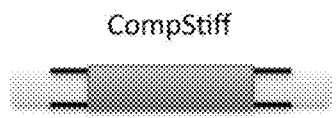
Figures 3, 11A:
Figure 11B:
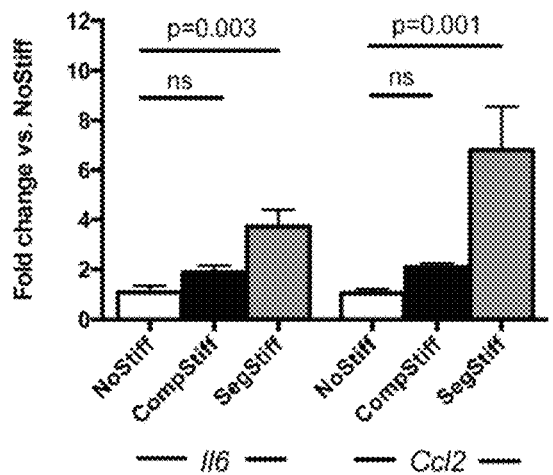
FIG. 11B is a bar graph depicting the differential expression of inflammation related genes Il6 and Ccl2 after one hour of mechanical stimulation of the three groups of aortas.
Figure 11C:
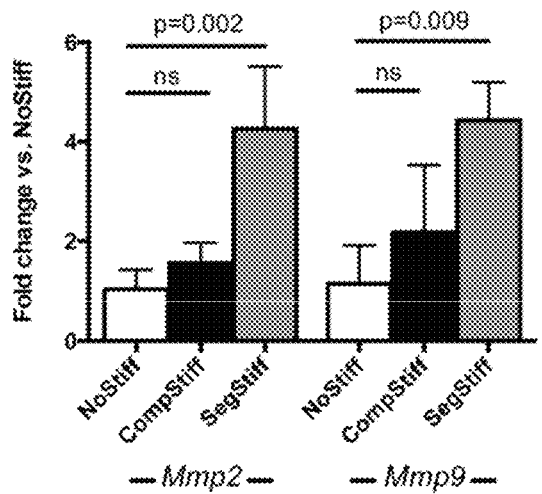
FIG. 11C is a bar graph depicting the differential expression of matrix metalloproteinases Mmp2 and Mmp9 after one hour of mechanical stimulation of the three groups of aortas.
Figure 11D:
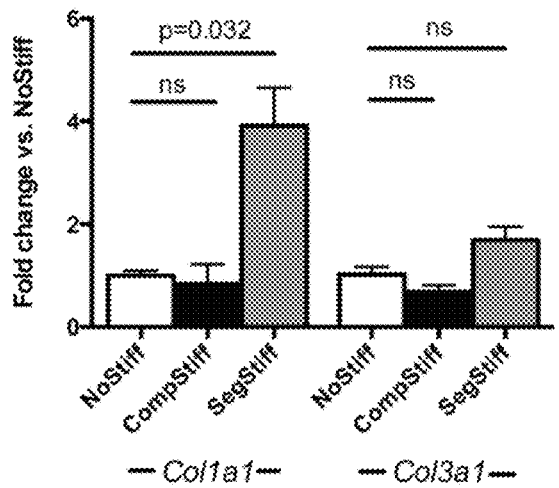
FIG. 11D is a bar graph depicting the differential expression of collagen genes Col1a1 and Col3a1 after one hour of mechanical stimulation of the three groups of aortas.

FIGS. 11A-1-11D depict ex vivo aortic mechanical stimulation. More specifically, FIGS. 11A-1, 11A-2, and 11A-3 depict the scheme of the experimental setup for differential mechanical stimulation of the cannulated aorta, in which cyclic strain is imposed on a unrestrained/unstiffened aorta (NoStiff) as shown in FIG. 11A-1, a completely restrained aorta (CompStiff) as shown in FIG. 11A-2, or a segmentally restrained aorta (SegStiff) as shown in FIG. 11A-3. FIG. 11B depicts the gene expression of inflammation related genes Il6 and Ccl2 after one hour of mechanical stimulation in the 3 groups. FIG. 11C depicts the gene expression of matrix metalloproteinases Mmp2 and Mmp9 after one hour of mechanical stimulation in the 3 groups. FIG. 11D depicts the gene expression of collagen genes Col1a1 and Col3a1 after one hour of mechanical stimulation in the 3 groups. In FIGS. 11B-11D, n=5 for each condition, and p values denote differences between treatment groups by Kruskal-Wallis test with Dunn's posttest.

Cuffing the entire aortic segment had minimal to no effect on the expression of inflammatory cytokines Il6 and Ccl2. Segmental stiffening, in contrast, induced upregulation of these genes, as shown in FIG. 11B. Likewise, the expression of metalloproteinases (Mmp2, Mmp9) as well as collagen genes (Col1a1, Col3a1)—quantified as indicators of active matrix remodeling—was significantly enhanced only in response to segmental stiffening, as shown in FIGS. 11C and 11D.

The results show that the aging human abdominal aorta exhibits segmental stiffening. In order to test whether SAS occurs naturally in the human aorta, the aortic stiffness was assessed in three distinct locations (suprarenal, mid-infrarenal, bifurcational) along the abdominal aortas of 19 male patients ranging in age from 36 to 71 years without evident AAA.

Figure 12A:
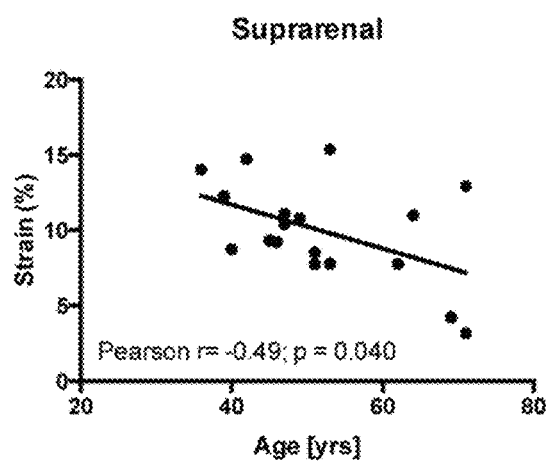
FIG. 12A is a scatter plot graph depicting the correlation between age and circumferential cyclic strain in the suprarenal segment of the human abdominal aorta.
Figure 12B:
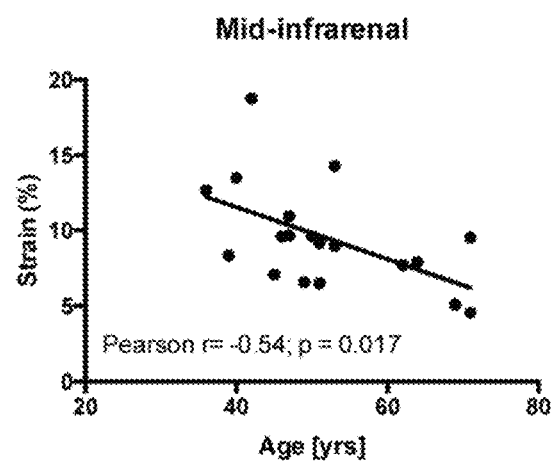
FIG. 12B is a scatter plot graph depicting the correlation between age and circumferential cyclic strain in the mid-infrarenal segment of the human abdominal aorta.
Figure 12C:
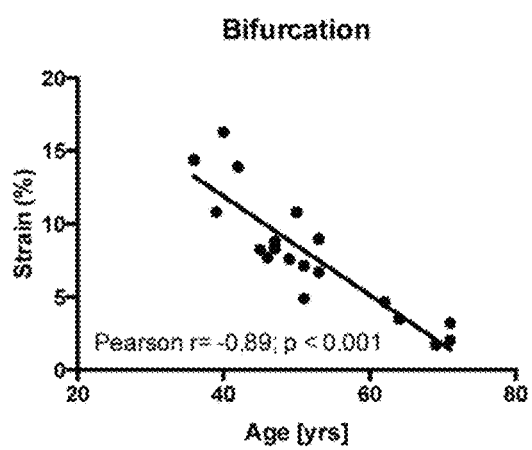
FIG. 12C is a scatter plot graph depicting the correlation between age and circumferential cyclic strain in the bifurcational segment of the human abdominal aorta.

As shown in FIGS. 12A-12C, a significant negative correlation was observed between age and aortic cyclic strain in the suprarenal and mid-infrarenal as well as in the aortic bifurcation segments, suggesting generally enhanced stiffness in the aging abdominal aorta.

Figure 12D:
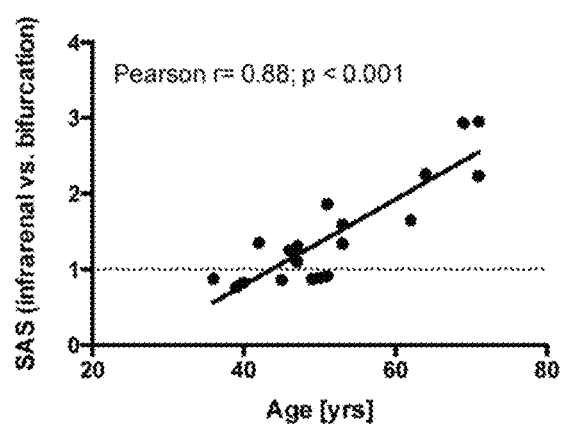
FIG. 12D is a scatter plot graph depicting the correlation between age and segmental stiffness (SAS, bifurcational segment vs. mid-infrarenal segment) along the infrarenal abdominal aorta.

Important differences between the distinct aortic locations were also detected. While both the mid-infrarenal aorta and the bifurcation exhibited age-related strain reduction, the slope of strain reduction was significantly steeper in the bifurcation segment, altering the (relative) SAS between two regions. In younger patients, the stiffness between both segments was similar (SAS-1), but doubled (SAS-2) by age 60, as shown in FIG. 12D. These results indicate that in addition to overall stiffening of the abdominal aorta with age, the human abdominal aorta exhibits age-related segmental stiffening.

FIGS. 12A-12D depict segmental aortic stiffening in the aging human abdominal aorta. More specifically, FIG. 12A depicts a correlation between age and circumferential cyclic strain in the supra-renal segment of the human abdominal aorta. FIG. 12B depicts a correlation between age and circumferential cyclic strain in the mid-infrarenal segment of the human abdominal aorta. FIG. 12C depicts a correlation between age and circumferential cyclic strain in the bifurcational segment of the human abdominal aorta. FIG. 12D depicts a correlation between age and segmental stiffness (SAS, bifurcational segment vs. mid-infrarenal segment) along the infrarenal abdominal aorta. In these figures, p denotes significance level of Pearson correlation.

DISCUSSION

Using an established murine elastase-induced AAA model, we demonstrated that segmental aortic stiffening (SAS) precedes aneurysm growth. Finite element analysis (FEA) revealed that early stiffening of the aneurysm-prone aortic segment leads to axial (longitudinal) wall stress generated by cyclic (systolic) tethering of adjacent, more compliant wall segments. Interventional stiffening of AAA-adjacent aortic segments (via external application of surgical adhesive) significantly reduced aneurysm growth. These changes correlated with reduced segmental stiffness of the AAA-prone aorta (due to equalized stiffness in adjacent segments), reduced axial wall stress, decreased production of reactive oxygen species (ROS), attenuated elastin breakdown, and decreased expression of inflammatory cytokines and macrophage infiltration, as well as attenuated apoptosis within the aortic wall. Cyclic pressurization of segmentally stiffened aortic segments ex vivo increased the expression of genes related to inflammation and extracellular matrix (ECM) remodeling. Finally, human ultrasound studies revealed that aging, a significant AAA risk factor, is accompanied by segmental infrarenal aortic stiffening.

Thus, the above example introduces the concept of segmental aortic stiffening (SAS) as an early pathomechanism generating aortic wall stress and triggering neurismal growth, thereby delineating a potential underlying molecular mechanisms and therapeutic targets. In addition, monitoring SAS may aid the identification of patients at risk for AAA.

AAA formation is accompanied by increased stiffness of the neurismal vessel segment compared to the normal aorta. Aneurysmal stiffening occurs due to profound changes in ECM organization including elastin fragmentation and enhanced adventitial collagen deposition and turnover. This example investigated aortic stiffening as a potential factor driving early AAA pathogenesis.

To explore the temporal relationship between aortic stiffening and AAA growth the widely-used PPE animal model was employed. As human AAA typically occurs in the aged aorta, which exhibits progressive elastin degeneration and stiffening, the PPE model was deliberately chosen as a non-dissection type preclinical model of AAA because it not only phenotypically resembles many aspects of the human disease but is also initiated by mild destruction of the elastin architecture (although this is achieved enzymatically by PPE perfusion in contrast to fatigue-related elastin fracture in the human situation). Moreover, previous studies indicated that this model in particular appears sensitive to extracellular matrix/stiffness related interventions. See Maegdefessel L, Azuma J, Toh R, Merk D, Deng A, Chin J, Raaz U, Schoelmerich A, Raiesdana A, Leeper N, McConnell M, Dalman R, Spin J, Tsao P, "Inhibition of microRNA-29b reduces murine abdominal aortic aneurysm development," *J Clin Invest.* 2012; 122:497-506.

The data in this example confirm that aortic stiffening precedes neurismal dilation. The rapid stiffening which occurred within one day after treatment seems to be due to early PPE-induced elastin damage, as shown in FIG. 6F. However, PPE is biologically active for no more than 24 hours after perfusion. Therefore, later structural alterations of the aorta, including the pervasive elastin fragmentation observed after 14 days as shown in FIG. 9F, appear to be PPE-independent.

Although the observed early and sustained stiffening of the aneurysm-prone aorta may seem counterintuitive, this finding supports aneurysm growth as an active process, as opposed to simple passive dilation. Moreover, segmental stiffening of the abdominal aorta may qualify as a mechanism generating wall stress.

Mechanical stress is a potent inducer of physiologic arterial remodeling. High flow-induced shear stress, elevated circumferential stress, and increased axial stress result in increased vessel diameter, wall thickening, and arterial lengthening, respectively, to achieve stress normalization. From a pathogenic point of view, mechanical forces induce a multitude of adverse events contributing to vascular disease, including ROS generation, apoptosis, and inflammation.

To test the hypothesis that SAS generates wall stress that precedes and triggers early AAA growth, in silico stress-analysis employing a FEA model was carried out. Inclusion of a stiff segment in a more compliant aorta generates axial stress under systolic pressurization. Axial stress increases with enhanced stiffness-gradients between stiff and non-stiff segments, as shown in FIG. 7A. Hypertension, a known AAA-associated risk factor, further increases axial stress in the setting of SAS, as shown in FIG. 7B. Of note, this simplified model only takes into account static wall stresses, neglecting dynamic effects that may occur due to cyclic systolic-diastolic wall deformations.

In the animal model in this Example, the peak of SAS at d7 coincided with the onset of accelerated neurismal enlargement. Delayed AAA formation until 7 days after PPE-treatment is consistent with the initial characterization of this model. The relationship between increasing SAS and subsequent neurismal dilation was further strengthened by a positive correlation between the extent of SAS at d7, and aortic diameter enlargement between d7 and d14.

To clarify the pathophysiologic significance of SAS for AAA-growth, rapid-hardening biologic glue was selectively applied to the aortic segments adjacent to the PPE-injury site, achieving dramatic stiffening of the adjacent aorta, detectable within one day after intervention. Subsequently, the relative segmental stiffness of the PPE-treated aorta compared to its adjacent segments (i.e, SAS) was instantly and permanently reduced. A major finding of this study is that the (glue-induced) reduction in SAS translated into significantly reduced AAA growth. In a more therapeutic context, it was additionally found that delayed glue application (day 7 post PPE injury) reduced subsequent AAA progression.

To elucidate the mechanisms of this process, factors that contribute to AAA and that are moreover known to be mechanosensitive were analyzed: ROS generation, inflammation, ECM-remodeling and apoptosis. ROS levels are locally increased in human AAA compared to the adjacent non-aneurysmal aorta. ROS may be generated in response to mechanical stress in endothelial cells (Ecs) as well as in vascular smooth muscle cells (VSMCs), whereby mechanically activated NADPH oxidases (NOX) and the mitochondrial electron transport chain seem to be significant sources. Mechanically generated ROS may subsequently trigger a variety of cellular responses such as VSMC apoptosis and vascular inflammation. ROS-scavengers and NADPH-oxidase inhibition have reduced oxidative stress and aortic macrophage infiltration, and ultimately ameliorated aneurysm growth or decreased aneurysm rupture incidence in various murine AAA models. Decreased ROS generation was found following glue-mediated reduction of SAS and axial stress.

AAA-formation is characterized by inflammatory remodeling of the aortic wall, and vascular inflammatory reactions are sensitive to mechanical stress-induced signaling. For example, mechanical stress induced pro-inflammatory mechanisms involve enhanced cytokine production via Ras/Rac1-p38-MAPK-NF-$\square$B (leading to enhanced IL-6 expression in VSMC), as well as enhanced NF-$\square$B-dependent expression of vascular chemokines and adhesion molecules that facilitate monocyte adhesion to the vascular wall. Interestingly, inflammatory cells such as monocytes/macrophages become mechanosensitive once attached to the vascular ECM. It has been shown that interventional stiffening of the adjacent aorta decreases macrophage infiltration in the aneurysm-prone (PPE-treated) segment and reduces the aortic and macrophage-specific expression of various inflammatory cytokines that are known to be critical for AAA pathogenesis, including Il1b, Il6 and Ccl2.

ECM remodeling, with enzymatic breakdown of matrix macromolecules mediated by the metalloproteinases MMP-2 and MMP-9, is another hallmark of AAA. MMP expression is increased in human AAA, and knockout of MMP-2 and MMP9 abolishes experimental AAA formation. MMP-2 and MMP-9 are also responsive to mechanical stress due to cyclic stretch and enhanced flow. More importantly, axial stress induces tissue remodeling and Mmp-2 activation in a model of longitudinal carotid growth. As expected, Mmp2 and Mmp9 were significantly upregulated in PPE-treated aorta, as shown in FIG. 10I. Reducing SAS, and thereby cyclic axial stress, with glue-stiffening reduced expression of both MMPs.

VSMC apoptosis is another critical feature of human and experimental AAA, and susceptible to enhanced mechanical (axial) stress. Signaling mechanisms of mechanical stress-induced VSMC apoptosis include a variety of molecules, such as the endothelin B receptor, integrinal -rac-p38-p53 signaling or Bcl-2-associated death factor (BAD). Enhanced medial layer apoptosis was identified in PPE-treated segments, which was decreased by glue-mediated axial stress reduction.

The impact of SAS on inflammation and matrix remodeling ex vivo was further investigated. Segmental stiffening (induced with an external cuff around the cyclically-pressurized aorta) resulted in significant upregulation of Mmp2 and Mmp9, Coital and Col3a1, as well as Il6 and Ccl2. In contrast to the in vivo situation, where enhanced bi-axial stiffness results from alterations of the inherent material properties of the vessel wall, the ex vivo model only simulated circumferential stiffening by external cuffing. Due to technical limitations, the systolic and diastolic pressure levels alternated with a frequency of 3/min (normal C57BL/6 heart rate:~450/min[41]). Nevertheless, the data indicate that cyclic axial mechanical stress may directly control genes governing inflammation and matrix remodeling.

Stiffening of the aneurysm-adjacent aorta was observed at d14 after PPE-induction, with subsequent reduction of aneurysm growth rate. This might represent an endogenous compensatory mechanism to reduce SAS and contain AAA progression. The stiffening process was paralleled by an enhanced fibrotic response in the AAA-adjacent segments' media, including upregulated collagen expression. A previous study showed that microRNA (miR)-29b is a repressor of collagen expression in AAA. See Maegdefessel L, Azuma J, Toh R, Merk D, Deng A, Chin J, Raaz U, Schoelmerich A, Raiesdana A, Leeper N, McConnell M, Dalman R, Spin J, Tsao P, "Inhibition of microRNA-29b reduces murine abdominal aortic aneurysm development," *J Clin Invest.* 2012; 122:497-506. Analogous miR-29b downregulation was identified in the (VSMC-dominated) media of the AAA-adjacent aortic segments, consistent with miR29b-modulated VSMC collagen production and medial fibrosis. It was previously demonstrated in the previous study mentioned immediately above that forced miR-29b downregulation (via systemic "anti-miR" administration) is a pro-fibrotic intervention reducing AAA growth. This reduction, in light of the present example, may be partially due to accelerated miR-29b-dependent stiffening of the AAA-adjacent aorta.

Local aortic PPE infusion is a widely used preclinical AAA model that exhibits many features seen in human AAA, including early disturbance of elastin integrity. However, due to the artificial, invasive nature of the model, including enzymatic injury of the vessel, segmental stiffness might be model-specific, and not a feature of human AAA. Therefore, it was further examined whether the human abdominal aorta exhibits segmental stiffness that would be a contributing factor for AAA formation. Performing ultrasound-based strain analyses in three distinct locations along the abdominal aorta (suprarenal, mid-infrarenal, bifurcation), age-dependent reduction of strain (increased stiffness) was detected, corresponding to previous observations (see O'Rourke M, Hashimoto J., "Mechanical factors in arterial aging: a clinical perspective," *J Am Coll Cardiol.* 2007; 50:1-13). As a novel finding, relatively more pronounced stiffening of the aortic bifurcation segment with age was detected as shown in FIG. 12C, translating into increasing SAS of the aortic bifurcation over time, as shown in FIG. 12D. This distal part of the aorta has relatively low elastin content as compared to the more proximal segments, a feature that might become functionally relevant with age-dependent loss of elastin. These data confirm and refine previous observations of enhanced age-dependent stiffening of the abdominal aorta and might partly explain the significant influence of age on AAA risk.

Of note, the segmental stiffness observed in the human abdominal aorta (SAS-2) was significantly smaller than the peak segmental stiffness in the PPE-treated aorta (SAS-5). The study patients presumably exhibited "physiologic" stiffness segmentation that will most likely not result in AAA formation. However, segmental stiffening may have more dramatic effects in individuals with genetic predilection for aneurysm formation.

Figure 19:
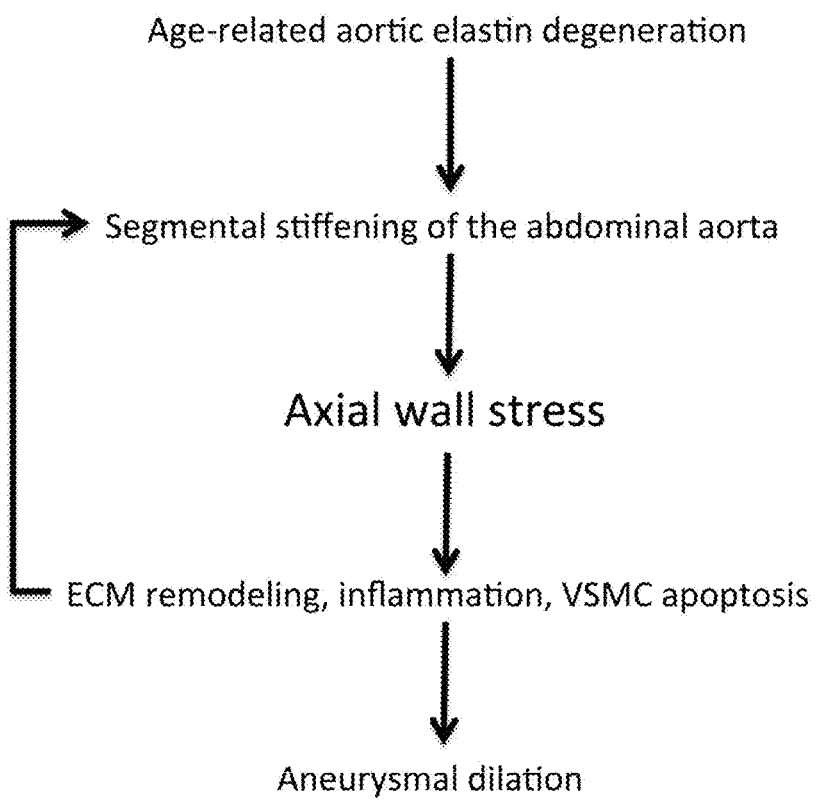
FIG. 19 is a flow chart describing the mechanism of early AAA formation driven by age-related segmental aortic stiffening, according to one embodiment.

In conclusion, the present example introduces the novel concept of segmental aortic stiffening as a pathogenetic factor contributing to AAA. It is proposed that degenerative stiffening of the aneurysm-prone aortic wall leads to axial stress, generated by cyclic tethering of adjacent, more compliant wall segments. Axial stress then induces and augments processes necessary for AAA growth such as inflammation and vascular wall remodeling, as shown in FIG. 19. More specifically, FIG. 19 depicts a proposed mechanism of early AAA formation driven by age-related segmental aortic stiffening. Degenerative segmental stiffening of the abdominal aorta induces axial stress in the stiff segment, thereby promoting active inflammatory wall remodeling resulting in AAA formation.

From a therapeutic perspective, this example shows that mechanically stiffening the AAA-adjacent aorta can provide a "stress shield" to limit AAA remodeling and expansion. While it could be postulated that protective interventional stiffening of an AAA-adjacent segment may create a distal stiffness gradient along the arterial tree that potentially triggers distal aneurysm formation, no evidence of this was observed during the 28-day time course of the instant model. This may indicate that in addition to stiffness gradients other predisposing co-factors (e.g., a structurally impaired vessel matrix) may be required to trigger AAA formation de novo. Further, increased blood pressure levels were not detected after interventional stiffening of the abdominal aorta that could potentially point towards negative hemodynamic side effects (See Table S1 below).

TABLE S1

Blood Pressure Measurements in Glue- or Sham-Treated Mice 7 Days after PPE-Induction

|  | Glue (n = 5) | Sham (n = 5) | p value |
| --- | --- | --- | --- |
| SBP | 128 ± 2 | 127 ± 3 | 0.627 |
| DBP | 100 ± 3 | 105 ± 3 | 0.826 |
| MAP | 110 ± 3 | 113 ± 3 | 0.888 |
| PP | 27 ± 2 | 25 ± 2 | 0.948 |

SBP indicates systolic blood pressure, DBP diastolic blood pressure, MAP mean arterial pressure, PP pulse pressure (= SBP − DBP).

All publications, patents and patent applications cited herein, whether supra or infra, are hereby incorporated by reference in their entireties.

It is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Although the present invention has been described with reference to preferred embodiments, persons skilled in the art will recognize that changes may be made in form and detail without departing from the spirit and scope of the invention.

What is claimed is:

1. A method of treating a vascular aneurysm in an artery, the method comprising positioning a support along at least a portion of at least one vascular segment adjacent to the vascular aneurysm to increase a mechanical stiffness of the at least one vascular segment.

2. The method of claim 1, wherein the positioning the support comprises applying a surgical adhesive to the at least one vascular segment.

3. The method of claim 1, wherein the positioning the support comprises implanting an intravascular stent at the at least one vascular segment.

4. The method of claim 1, wherein growth of the vascular aneurysm following the increased mechanical stiffening of the at least one vascular segment is reduced relative to growth of the vascular aneurysm in the absence of the increased mechanical stiffening of the at least one vascular segment.

5. The method of claim 1, wherein inflammation in the artery following the increased mechanical stiffening of the at least one vascular segment is reduced relative to inflammation in the artery in the absence of the increased mechanical stiffening of the at least one vascular segment.

6. The method of claim 1, wherein apoptosis in the artery following the increased mechanical stiffening of the at least one vascular segment is reduced relative to apoptosis in the artery in the absence of the increased mechanical stiffening of the at least one vascular segment.

7. The method of claim 1, wherein production of reactive oxygen species in the artery following the increased mechanical stiffening of the at least one vascular segment is reduced relative to production of reactive oxygen species in the artery in the absence of the increased mechanical stiffening of the at least one vascular segment.

8. The method of claim 1, wherein the vascular aneurysm is an early stage vascular aneurysm.

9. The method of claim 1, wherein the at least one vascular segment comprises a vascular segment upstream of the vascular aneurysm or a vascular segment downstream of the vascular aneurysm.

10. The method of claim 1, wherein the at least one vascular segment comprises a vascular segment upstream of the vascular aneurysm and a vascular segment downstream of the vascular aneurysm.

11. The method of claim 1, wherein the mechanical stiffness is increased in a targeted manner, thereby treating the vascular segment.

12. The method of claim 1, wherein the support is a physical structure applied within or outside of the at least one vascular segment.

13. A method of minimizing growth of a vascular aneurysm in an artery, the method comprising selectively increasing a mechanical stiffness of at least one vascular segment adjacent to the vascular aneurysm such that the vascular aneurysm is not directly treated.

14. The method of claim 13, wherein selectively increasing the mechanical stiffness of the at least one vascular segment comprises applying a surgical adhesive to the at least one vascular segment.

15. The method of claim 13, wherein growth of the vascular aneurysm following the increased mechanical stiffening of the at least one vascular segment is reduced relative to growth of the vascular aneurysm in the absence of the increased mechanical stiffening of the at least one vascular segment.

16. The method of claim 13, wherein inflammation in the artery following the increased mechanical stiffening of the at least one vascular segment is reduced relative to inflammation in the artery in the absence of the increased mechanical stiffening of the at least one vascular segment.

17. The method of claim 13, wherein apoptosis in the artery following the increased mechanical stiffening of the at least one vascular segment is reduced relative to apoptosis in the artery in the absence of the increased mechanical stiffening of the at least one vascular segment.

18. The method of claim 13, wherein production of reactive oxygen species in the artery following the increased mechanical stiffening of the at least one vascular segment is reduced relative to production of reactive oxygen species in the artery in the absence of the increased mechanical stiffening of the at least one vascular segment.

19. The method of claim 13, wherein the vascular aneurysm is an early stage vascular aneurysm.

20. The method of claim 13, wherein selectively increasing the mechanical stiffness of the at least one vascular segment comprises implanting an intravascular stent at the at least one vascular segment.

21. The method of claim 13, wherein the at least one vascular segment comprises a vascular segment upstream of the vascular aneurysm or a vascular segment downstream of the vascular aneurysm.

22. A method of treating a vascular aneurysm, the method comprising increasing a mechanical stiffness of at least one aneurysm-adjacent vascular segment by positioning a stiffening device or stiffening composition at the at least one aneurysm-adjacent vascular segment and not at the vascular aneurysm.

23. The method of claim 22, wherein the stiffening composition comprises a surgical adhesive, and wherein the positioning the stiffening device or the stiffening composition comprises applying the surgical adhesive to an outer surface of the aneurysm-adjacent vascular segment.

24. The method of claim 22, wherein the stiffening device comprises an intravascular stent, and wherein the positioning the stiffening device or the stiffening composition comprises deploying the intravascular stent into a lumen of the aneurysm-adjacent vascular segment.

25. The method of claim 22, wherein the at least one aneurysm-adjacent vascular segment is upstream of the vascular aneurysm or downstream of the vascular aneurysm.

* * * * *